US010744277B2

(12) United States Patent
Finke et al.

(10) Patent No.: US 10,744,277 B2
(45) Date of Patent: Aug. 18, 2020

(54) AEROSOL DELIVERY DEVICE AND METHOD OF OPERATING THE AEROSOL DELIVERY DEVICE

(71) Applicant: PARI Pharma GmbH, Starnberg (DE)

(72) Inventors: Matthias Finke, Munich (DE); Dominique Mutschmann, Munich (DE); Wolfgang Achtzehner, Alling (DE); Philipp Holzmann, Munich (DE)

(73) Assignee: PARI Pharma GmbH, Starnberg (DE)

( * ) Notice: Subject to any disclaimer, the term of this patent is extended or adjusted under 35 U.S.C. 154(b) by 723 days.

(21) Appl. No.: 15/104,109

(22) PCT Filed: Dec. 15, 2014

(86) PCT No.: PCT/EP2014/077753
§ 371 (c)(1),
(2) Date: Jun. 13, 2016

(87) PCT Pub. No.: WO2015/091356
PCT Pub. Date: Jun. 25, 2015

(65) Prior Publication Data
US 2016/0310681 A1 Oct. 27, 2016

(30) Foreign Application Priority Data
Dec. 16, 2013 (EP) .................................... 13197391

(51) Int. Cl.
*A61M 11/00* (2006.01)
*A61M 15/00* (2006.01)
(Continued)

(52) U.S. Cl.
CPC ...... *A61M 11/005* (2013.01); *A61M 15/0021* (2014.02); *A61M 15/0085* (2013.01);
(Continued)

(58) Field of Classification Search
CPC ................................................. G06K 9/00536
See application file for complete search history.

(56) References Cited

U.S. PATENT DOCUMENTS 6,901,926 B2   6/2005  Yamamoto et al.
8,720,432 B2   5/2014  Borgschulte et al.
(Continued)

FOREIGN PATENT DOCUMENTS

DE    295 01 569 U1   4/1995
DE    19953317 C1     2/2001
(Continued)

OTHER PUBLICATIONS

Michaels, Jennifer E., et al., "A comparison of feature-based classifiers for ultrasonic structural health monitoring", SPIE Proceedings, vol. 5394, Health Monitoring and Smart Nondestructive Evaluation of Structural and Biological Systems III, T. Kundu Ed., Jul. 21, 2004, pp. 363-374.
(Continued)

*Primary Examiner* — Rachel T Sippel
(74) *Attorney, Agent, or Firm* — Wolf, Greenfield & Sacks, P.C.

(57) ABSTRACT

An aerosol delivery device includes an aerosol generator for generating an aerosol in the aerosol delivery device with a membrane and a vibrator which is configured to vibrate a fluid and to aerosolise the fluid by the membrane. The aerosol delivery device further includes a fluid reservoir for receiving the fluid to be aerosolised, the fluid reservoir being arranged in fluid communication with the membrane, a controller which is configured to sequentially operate the vibrator at a plurality of different vibration frequencies, a sensor which is configured to detect at least one electrical parameter of the vibrator for each of the plurality of different vibration frequencies, and a detector which is configured to detect the presence of fluid in contact with the membrane
(Continued)

and/or in the fluid reservoir on the basis of the dependence of the detected values of the at least one electrical parameter on the vibration frequency.

19 Claims, 5 Drawing Sheets

(51) Int. Cl.
  *B05B 17/00*   (2006.01)
  *G06K 9/00*    (2006.01)
  *B05B 12/08*   (2006.01)
  *A61M 15/08*   (2006.01)

(52) U.S. Cl.
  CPC ........... *A61M 15/08* (2013.01); *B05B 12/081* (2013.01); *B05B 17/0638* (2013.01); *G06K 9/00536* (2013.01); *A61M 2205/18* (2013.01); *A61M 2205/3317* (2013.01); *A61M 2205/3386* (2013.01); *A61M 2205/582* (2013.01); *A61M 2205/583* (2013.01)

(56) References Cited

U.S. PATENT DOCUMENTS

| | | | |
|---|---|---|---|
| 2002/0129813 A1 | 9/2002 | Litherland et al. | |
| 2006/0102172 A1 | 5/2006 | Feiner et al. | |
| 2007/0277816 A1 | 12/2007 | Morrison et al. | |
| 2008/0064965 A1 | 3/2008 | Jay et al. | |
| 2009/0056708 A1 | 3/2009 | Stenzler et al. | |
| 2009/0240192 A1 | 9/2009 | Power et al. | |
| 2015/0231340 A1* | 8/2015 | Pumphrey | B06B 1/0284 128/200.16 |
| 2015/0320944 A1* | 11/2015 | Grehan | B05B 15/14 73/658 |

FOREIGN PATENT DOCUMENTS

| | | |
|---|---|---|
| DE | 10 2005 006372 B4 | 8/2006 |
| DE | 10 2008 054431 B3 | 6/2010 |
| EP | 1227856 | 8/2002 |
| EP | 1558315 A1 | 8/2005 |
| EP | 2047914 A1 | 4/2009 |
| EP | 2361108 | 8/2011 |
| JP | 2000-176014 A | 6/2000 |
| JP | 2009-095228 A | 4/2009 |
| WO | WO 2001/34232 A1 | 5/2001 |
| WO | WO 2004/039442 A1 | 5/2004 |
| WO | WO 2006/094796 A1 | 9/2006 |
| WO | WO 2010/066714 A1 | 6/2010 |
| WO | WO 2014-062175 A1 | 4/2014 |
| WO | WO 2015-010809 A1 | 1/2015 |

OTHER PUBLICATIONS

European Examination Report dated Jan. 30, 2018 in connection with European Application No. 14815314.1.

\* cited by examiner

AEROSOL DELIVERY DEVICE AND METHOD OF OPERATING THE AEROSOL DELIVERY DEVICE

FIELD OF THE INVENTION

The invention relates to an aerosol delivery device comprising an aerosol generator with a membrane and a vibrator configured to vibrate a fluid and to aerosolise the fluid by the membrane and to a method of operating this aerosol delivery device.

BACKGROUND ART

Aerosols for therapeutic purposes are generated and delivered to a desired location within a user's or patient's body with aerosol delivery devices. A fluid or liquid (i.e., medicament) to be aerosolised or nebulised is supplied to an aerosol generator of the aerosol delivery device, the fluid or liquid is aerosolised or nebulised by the aerosol generator and the resultant aerosol is supplied to the user or patient.

The fluid or liquid may be aerosolised or nebulised in the aerosol generator by a membrane with through holes. The fluid or liquid may be in contact with the membrane via gravitational force or a supply system. The fluid or liquid may be supplied via a supply system as e.g. a vibratable slide, vibratable plunger, vibratable wall and/or vibratable membrane.

The membrane may be a passive or an active membrane. In the case that the membrane is not vibrated by a vibrator, it is a passive membrane. The passive membrane may include a supply system and have e.g. a vibrator in contact with the fluid reservoir, wall, channel plunger, and/or supply system.

In the case when the membrane is vibrated by a vibrator, it is an active membrane.

An inhalation nebuliser of this passive membrane type is disclosed in U.S. Pat. No. 6,901,926 B2 as well as in US 2004/0045547 A1, which describe e.g. the nebulisers (inhalers) U1 and U22 from the company Omron. Further inhalation nebulisers of the passive membrane type are disclosed in US 121183747, WO 2006/094796 as well as in US 2009/0056708, which describe the Fox-POP, Medspray and Telemaq nebuliser technology. A further existing aerosol generator with a cantilever concept is disclosed in EP 0432992 A1 from the company Bespak.

An inhalation nebuliser of this active (vibrating) membrane type is disclosed in DE 199 53 317 C1, which describes e.g. the eFlow inhalation device from the company PARI. The aerosol membrane generator described in this document comprises a cylindrical liquid storage container which is delimited at one end face by a membrane having the shape of a circular disc. A liquid disposed in the liquid storage container contacts the side of the membrane facing the container.

DE 199 53 317 C1 further discloses an oscillation generator, for example, a piezocrystal, which surrounds the membrane in a circular manner and is connected thereto such that the membrane can be caused to oscillate by means of the oscillation generator and an electric drive circuit. The liquid abutting the membrane on the one side is conveyed through holes in the oscillating membrane to the other side of the membrane and is emitted on this side into a mixing chamber as an aerosol.

Known from the utility model DE 295 01 569 is an ultrasonic liquid nebuliser having a piezocrystal which is caused to oscillate electrically by an oscillator circuit, the oscillator circuit being supplied by a power supply device.

DE 295 01 569 describes an oscillator circuit which comprises a current limiting circuit and which is connected with an electronic temperature limiting circuit that compares a temperature-dependant electric signal occurring at the piezocrystal in a threshold circuit, the comparison signal of which activates a bistable circuit which blocks the oscillator when a limiting temperature in the piezocrystal is reached.

The disclosure of DE 295 01 569 is thereby directed at a protective mechanism for an ultrasonic liquid nebuliser in which the piezocrystal itself causes the liquid to oscillate and is in contact with a comparatively large amount of liquid. The liquid nebuliser described in DE 295 01 569 must furthermore accordingly use large currents in order to cause the large amount of liquid to oscillate.

Constant contact between the piezocrystal and the liquid is necessary owing to these large currents and the resulting large temperature differences in order to prevent destruction of the piezocrystal. If there is no longer any liquid present, the piezocrystal heats up very quickly and is destroyed if the oscillating circuit driving the nebuliser is not switched off immediately.

Only much smaller currents flow in inhalation nebulisers of the type described above, i.e. in inhalation nebulisers having membrane aerosol generators, and therefore only comparatively small temperature differences occur. In such inhalation nebulisers, the lack of liquid does not directly lead to heat-related damage to the piezoelectric elements. However, if a membrane inhalation nebuliser runs without a liquid (or fluid) load, this can, on rare occasions, cause the membrane to break.

However, it is also necessary in inhalation nebulisers having a membrane generator to reliably detect the presence of a liquid to be nebulised. This is because, on the one hand, the basis for a high dosage accuracy could be thereby created and, on the other hand, it is possible to reliably indicate the end of a therapy session to the patient. Normally it is desired to generate aerosol from the whole liquid to ensure the inhalation therapy success. Especially an early end of the therapy session, with remaining liquid in the reservoir, has to be avoided. In addition, when adherence to therapy is monitored with a patient in telemedicine applications, the signal provides assurance that the entire liquid volume and dose has been nebulised and delivered. Furthermore, by immediately disconnecting the inhalation therapy device, it is possible, for example, to save power, e.g. increasing the lifetime of a battery.

Therefore, the use of a protective mechanism such as described in DE 295 01 569 is not necessary in inhalation nebulisers of the type in question here and is not possible either owing to the much smaller currents and temperature alterations.

EP 1 558 315 A1 discloses an inhalation therapy device including a membrane aerosol generator. A detection device is provided for determining whether a liquid to be nebulised is available. Determination of whether liquid is present or not occurs in the detection device by comparing the detected value of an electrical parameter of the membrane aerosol generator with a value for this parameter stored in the detection device. For this purpose, the detection device may use empirically determined values for the detected electrical parameter or a value of the electrical parameter which was detected in a previous cycle. This determination process may be independently and separately performed at different measurement frequencies.

However, this approach of determining the presence of liquid in the membrane aerosol generator is sensitive to the structural details of the membrane aerosol generator, such as the thickness and bonding of the piezo-element, and susceptible to external influences, such as the surface tension and the temperature of the liquid to be nebulised and the pressure in the liquid reservoir. These factors can affect the determination accuracy, so that the presence or absence of liquid in the membrane aerosol generator may not be reliably identified.

Hence, there remains a need for an aerosol delivery device and an aerosol delivery method which allow for the presence of fluid or liquid to be aerosolised or nebulised to be reliably and efficiently detected.

SUMMARY OF THE INVENTION

One object of the invention is to provide an aerosol delivery device which enables reliable and efficient detection of the presence of fluid to be aerosolised in a fluid reservoir of the device. Further, the invention aims to provide a method of operating this aerosol delivery device.

The invention provides an aerosol delivery device comprising an aerosol generator for generating an aerosol in the aerosol delivery device with a membrane, e.g. a vibratable or oscillatable membrane, and a vibrator, vibration generator or oscillator which is configured to vibrate or oscillate a fluid and to aerosolise the fluid by the membrane. The aerosol delivery device further comprises a fluid or liquid reservoir for receiving the fluid or liquid to be aerosolised or nebulised, the fluid or liquid reservoir being arranged in fluid communication with the vibratable membrane, a controller which is configured to sequentially operate the vibrator, vibration generator or oscillator at a plurality of different vibration frequencies or oscillation frequencies and a sensor which is configured to detect, sense or measure at least one electrical parameter of the vibrator, vibration generator or oscillator for each of the plurality of different vibration frequencies or oscillation frequencies. Moreover, the aerosol delivery device comprises a detector which is configured to detect or determine the presence of fluid or liquid in contact with the membrane and/or in the fluid reservoir on the basis of the dependence of the detected values of the at least one electrical parameter, i.e., the values of the at least one electrical parameter detected by the sensor, on the vibration frequency or oscillation frequency.

Herein, the term "sequentially" defines that the controller is configured so that it operates the vibrator at consecutive or successive different vibration frequencies or oscillation frequencies. The controller is thus configured to sequentially vary a vibration frequency or oscillation frequency of the vibrator. The fluid is thus vibrated by the vibrator at a plurality of sequential, consecutive or successive different vibration frequencies or oscillation frequencies.

The detector is configured to detect or determine the presence of fluid in contact with the membrane and/or in the fluid reservoir, i.e., the presence of fluid to be aerosolised in the fluid reservoir. The detector is configured to detect or determine the presence of fluid in contact with the membrane and/or in the fluid reservoir on the basis of, e.g. by analysing, the dependence of the detected values of the at least one electrical parameter on the vibration frequency or oscillation frequency. The detector may be configured so that it detects or determines the presence of fluid in contact with the membrane and/or in the fluid reservoir on the basis of a curve, e.g. a measured, detected or sensed curve, of the detected values of the at least one electrical parameter as a function of or dependent on the vibration frequency or oscillation frequency.

Herein, the term "curve" defines a graph or trajectory which is obtained by giving, e.g. graphing or plotting, the detected values of the at least one electrical parameter as a function of or dependent on the vibration frequency or oscillation frequency. Adjacent or neighbouring detection points, i.e. adjacent or neighbouring detected values of the at least one electrical parameter, may be connected with each other, e.g. by straight and/or curved lines or splines. It is also possible to use approximations or polynomial functions as a curve from the at least one electrical parameter for the curve analyses, parameter analyses or comparisons.

By detecting the presence of fluid in contact with the membrane and/or in the fluid reservoir on the basis of the dependence of the detected values of the at least one electrical parameter on the vibration frequency, the frequency dependence of the at least one electrical parameter is taken into account in the detection process. The detection process is thus significantly less sensitive to changes in the signal characteristics of the at least one electrical parameter, in particular, phase shifts of the signal, as compared to detection processes in which detected parameter values are compared with empirically determined or previously detected values. In this way, the influence of the structural details of the aerosol generator and of external factors, such as the surface tension and the temperature of the fluid and the pressure in the fluid reservoir, which can considerably affect the signal characteristics, can be minimised, thus allowing for the presence of fluid in contact with the membrane and/or in the fluid reservoir to be detected or determined in a reliable and efficient manner.

The fluid or liquid reservoir may be arranged for directly receiving the fluid or liquid to be aerosolised. For example, the fluid or liquid reservoir may be configured as a fluid or liquid chamber or container into which a fluid or liquid can be directly filled.

Further, the fluid or liquid reservoir may be arranged for receiving a fluid or liquid containing vessel. In particular, the fluid or liquid reservoir may be designed so that it does not directly receive the fluid or liquid but rather has an opening element, such as a thorn, a spike, a hollow needle or the like, arranged on its inside that opens the fluid containing vessel, e.g., a vial, a blister, an ampoule, a container, a canister, a reservoir, a cartridge, a pot, a tank, a pen, a storage, a syringe or the like, inserted therein.

The detector may form part of the controller or may be provided as a separate unit or entity. The sensor may form part of the controller or may be provided as a separate unit or entity. The detector and the sensor may be provided as a combined unit or entity or as separate units or entities. The sensor and/or the detector may be connected to the controller. The detector and the sensor may be connected with each other.

The controller may be any type of controller, e.g., a control unit, a control element, a control circuit or the like, which is capable of operating the vibrator of the aerosol generator at a plurality of different vibration frequencies or oscillation frequencies. The controller may be connected to the vibrator, e.g. to a power supply element of the vibrator. The controller may communicate with the vibrator by wireless communication.

The aerosol delivery device may be configured so that the detection process is performed continuously or at discrete time intervals. In the latter case, the aerosol delivery process, i.e., the aerosol delivery to a patient or user, may be regularly or irregularly interrupted for preset, predefined or predetermined, e.g. regular or irregular, time intervals and the detection process, i.e. the operation of the vibrator at the plurality of different vibration frequencies, the detection of the at least one electrical parameter by the sensor and the detection of the presence of fluid by the detector, may be performed in these intervals.

The aerosol delivery device may be an aerosol generation device, an aerosol inhalation device, a medical aerosol device, an aerosol diagnostic device, an aerosol prophylactic device, an aerosol therapeutic device, an aerosol humidification device, an aerosol therapy device or the like.

The aerosol generator may be a nebuliser, such as a vibrating membrane nebuliser, e.g. an electronic vibrating membrane nebuliser, an atomiser or the like. In particular, the aerosol generator may be an electronic nebuliser, e.g., a piezo-electrically driven nebuliser, i.e., a nebuliser driven by a piezoelectric element. In this case, the piezoelectric element may form part of the vibrator and be arranged for vibrating or oscillating the fluid.

A fluid or liquid to be nebulised or aerosolised by the aerosol generator may be a fluid or liquid for the generation of a pharmaceutical aerosol for the delivery of an active compound.

An active compound is a natural, biotechnology-derived or synthetic compound or mixture of compounds useful for the diagnosis, prevention, management or treatment of a disease, condition or symptom of an animal, in particular a human. Other terms which may be used as synonyms of active compounds include, for example, active ingredient, active pharmaceutical ingredient, drug substance, diagnostic material, drug, medicament and the like. The fluid could be of a liquid, solution, suspension, colloidal mixture or liposomal formulation form and can be prepared, mixed or opened before or during the application.

The active compound comprised in the fluid to be nebulised or aerosolised by the aerosol generator may be a drug substance or a medicament which is useful for the prevention, management, diagnosis or treatment of any disease, symptom or condition affecting the body, skin, body cavities, the abdomen, the eyes, the ear, the intestine, the stomach, the nose, the sinuses, the osteomeatal complex, the mouth, the trachea, the lungs, upper lungs, lower lungs, central lungs, the bronchia, the bronchioles, the alveoli and/or the respiratory tract.

Among the active compounds which may be useful for serving one of the purposes named previously and that may be used together with the present invention, are, for example, substances selected from the group consisting of anti-inflammatory compounds, anti-infective agents, antiseptics, prostaglandins, endothelin receptor agonists, phosphodiesterase inhibitors, beta-2-sympathicomimetics, decongestants, vasoconstrictors, anticholinergics, immunomodulators, mucolytics, anti-allergic drugs, antihistaminics, mast-cell stabilizing agents, tumor growth inhibitory agents, wound healing agents, local anaesthetics, antioxidants, oligonucleotides, peptides, proteins, vaccines, vitamins, plant extracts, cholinesterase inhibitors, vasoactive intestinal peptide, serotonin receptor antagonists, and heparins, glucocorticoids, anti-allergic drugs, antioxidants, vitamins, leucotriene antagonists, anti-infective agents, antibiotics, antifungals, antivirals, mucolytics, decongestants, antiseptics, cytostatics, immunomodulators, vaccines, wound healing agents, local anaesthetics, oligonucleotides, xanthin derived agents, peptides, proteins and plant extracts. Such compound may be used in the form of a suspension, a solution, a colloidal formulation (i.e., liposomal), etc.

Examples of potentially useful anti-inflammatory compounds are glucocorticoids and non-steroidal anti-inflammatory agents such as betamethasone, beclomethasone, budesonide, ciclesonide, dexamethasone, desoxymethasone, fluoconolone acetonide, fluocinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, dehydroepiandrosterone-sulfate (DHEAS), elastane, prostaglandin, leukotriene, bradykinin antagonists, non-steroidal anti-inflammatory drugs (NSAIDs), such as ibuprofen including any pharmaceutically acceptable salts, esters, isomers, stereoisomers, diastereomers, epimers, solvates or other hydrates, prodrugs, derivatives, or any other chemical or physical forms of active compounds comprising the respective active moieties.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amiidine penicillins (mecillinam);

cephalosporins, including cefazolins (cefazolin, cefazedone); cefuroximes (cefuroxim, cefamandole, cefotiam), cefoxitins (cefoxitin, cefotetan, latamoxef, flomoxef), cefotaximes (cefotaxime, ceftriaxone, ceftizoxime, cefmenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetil, cefuroxime axetil, cefetamet pivoxil, cefotiam hexetil), loracarbef, cefepim, clavulanic acid/amoxicillin, Ceftobiprole;

synergists, including beta-lactamase inhibitors, such as clavulanic acid, sulbactam, and tazobactam;

carbapenems, including imipenem, cilastin, meropenem, doripenem, tebipenem, ertapenem, ritipenam, and biapenem;

monobactams, including aztreonam;

aminoglycosides, such as apramycin, gentamicin, amikacin, isepamicin, arbekacin, tobramycin, netilmicin, spectinomycin, streptomycin, capreomycin, neomycin, paromoycin, and kanamycin;

macrolides, including erythromycin, clarythromycin, roxithromycin, azithromycin, dithromycin, josamycin, spiramycin and telithromycin;

gyrase inhibitors or fluroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin;

tetracyclins, including tetracyclin, oxytetracyclin, rolitetracyclin, minocyclin, doxycycline, tigecycline and aminocycline;

glycopeptides, including vancomycin, teicoplanin, ristocetin, avoparcin, oritavancin, ramoplanin, and peptide 4;

polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;

sulfonamides, including sulfadiazine, sulfamethoxazole, sulfalene, co-trimoxazole, co-trimetrol, co-trimoxazine, and co-tetraxazine;

azoles, including clotrimazole, oxiconazole, miconazole, ketoconazole, itraconazole, fluconazole, metronidazole, tinidazole, bifonazol, ravuconazol, posaconazol, voriconazole, and ornidazole and other antifungals including flucytosin, griseofulvin, tolnaftal, naftifin, terbinafin, amorolfin, ciclopiroxolamin, echinocandins, such as micafungin, caspofungin, anidulafungin;

nitrofurans, including nitrofurantoin and nitrofuranzone;

polyenes, including amphotericin B, natamycin, nystatin, flucytosine;

other antibiotics, including tithromycin, lincomycin, clindamycin, oxazolindiones (linzezolids), ranbezolid, streptogramine A+B, pristinamycin A+B, Virginiamycin A+B, dalfopristin/quinupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, clerocidin, filgrastim, and pentamidine;

antivirals, including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabine, tromantadine, and proteinase inhibitors, siRNA based drugs;

antiseptics, including acridine derivatives, iodine-povidone, benzoates, rivanol, chlorhexidine, quarternary ammonium compounds, cetrimides, biphenylol, clorofene, and octenidine;

plant extracts or ingredients, such as plant extracts from chamomile, hamamelis, echinacea, calendula, thymian, papain, pelargonium, pine trees, essential oils, myrtol, pinen, limonen, cineole, thymol, mentol, camphor, tannin, alpha-hederin, bisabolol, lycopodin, vitapherole;

wound healing compounds including dexpantenol, allantoin, vitamins, hyaluronic acid, alpha-antitrypsin, anorganic and organic zinc salts/compounds, salts of bismuth and selen;

interferons (alpha, beta, gamma), tumor necrosis factors, cytokines, interleukines;

immunmodulators including methotrexat, azathioprine, cyclosporine, tacrolimus, sirolimus, rapamycin, mofetil; mofetil-mycophenolate;

cytostatics and metastasis inhibitors;

alkylants, such as nimustine, melphanlane, carmustine, lomustine, cyclophosphamide, ifosfamide, trofosfamide, chlorambucil, busulfane, treosulfane, prednimustine, thiotepa;

antimetabolites, e.g. cytarabine, fluorouracil, methotrexate, mercaptopurine, tioguanine;

alkaloids, such as vinblastine, vincristine, vindesine;

antibiotics, such as alcarubicine, bleomycine, dactinomycine, daunorubicine, doxorubicine, epirubicine, idarubicine, mitomycine, plicamycine;

complexes of transition group elements (e.g. Ti, Zr, V, Nb, Ta, Mo, W, Pt) such as carboplatinum, cis-platinum and metallocene compounds such as titanocendichloride;

amsacrine, dacarbazine, estramustine, etoposide, beraprost, hydroxycarbamide, mitoxanthrone, procarbazine, temiposide;

paclitaxel, gefitinib, vandetanib, erlotinib, poly-ADP-ribose-polymerase (PRAP) enzyme inhibitors, banoxantrone, gemcitabine, pemetrexed, bevacizumab, ranibizumab.

Examples of potentially useful mucolytics are DNase, P2Y2-agonists (denufosol), drugs affecting chloride and sodium permeation, such as N-(3,5-Diamino-6-chloropyrazine-2-carbony)-N'-{4-[4-(2,3-dihydroxypropoxy)-phenyl]butyl}guanidine methanesulfonate (PARION 552-02), heparinoids, guaifenesin, acetylcysteine, carbocysteine, ambroxol, bromhexine, tyloxapol, lecithins, myrtol, and recombinant surfactant proteins.

Examples of potentially useful vasoconstrictors and decongestants which may be useful to reduce the swelling of the mucosa are phenylephrine, naphazoline, tramazoline, tetryzoline, oxymetazoline, fenoxazoline, xylometazoline, epinephrine, isoprenaline, hexoprenaline, and ephedrine.

Examples of potentially useful local anaesthetic agents include benzocaine, tetracaine, procaine, lidocaine and bupivacaine.

Examples of potentially useful antiallergic agents include the afore-mentioned glucocorticoids, cromolyn sodium, nedocromil, cetrizin, loratidin, montelukast, roflumilast, ziluton, omalizumab, heparinoids and other antihistamins, including azelastine, cetirizin, desloratadin, ebastin, fexofenadin, levocetirizin, loratadin.

Examples of potentially useful anticholinergic agents include ipratropium bromide, tiotropium bromide, oxitropium bromide, glycopyrrolate.

Examples of potentially useful beta-2-sympathicomimetic agents include salbutamol, fenoterol, formoterol, indacaterol, isoproterenol, metaproterenol, salmeterol, terbutaline, clenbuterol, isoetarine, pirbuterol, procaterol, ritodrine.

Examples of xanthine derived agents include theophylline, theobromine, caffeine.

Antisense oligonucleotides are short synthetic strands of DNA (or analogs) that are complimentary or antisense to a target sequence (DNA, RNA) designed to halt a biological event, such as transcription, translation or splicing. The resulting inhibition of gene expression makes oligonucleotides dependent on their composition useful for the treatment of many diseases and various compounds are currently clinically evaluated, such as ALN-RSV01 to treat the respiratory syncytical virus by, AVE-7279 to treat asthma and allergies, TPI-ASM8 to treat allergic asthma, 1018-ISS to treat cancer. Examples of potentially useful peptides and proteins include antibodies against toxins produced by microorganisms, antimicrobial peptides such as cecropins, defensins, thionins, and cathelicidins.

The detector may be configured to detect the presence of fluid or liquid in contact with the membrane and/or in the fluid reservoir on the basis of a cross correlation of a curve of the detected values of the at least one electrical parameter as a function of or dependent on the vibration frequency with a reference curve.

A cross correlation is a mathematical operation which provides a measure of the similarity of two curves. The reference curve may be a curve of characteristic values of the at least one electrical parameter as a function of the vibration frequency. For example, the reference curve may be obtained by performing a plurality of detections or measurements of the at least one electrical parameter as a function of the vibration frequency, e.g. 10 to 60 detections or measurements, and taking the mean or average value of the at least one electrical parameter at each vibration frequency for this plurality of detections or measurements. The reference curve may represent characteristic values of the at least one electrical parameter for the case that fluid in contact with the membrane and/or in the fluid reservoir is present or may represent characteristic values of the at least one electrical parameter for the case that no fluid in contact with the membrane and/or in the fluid reservoir is present.

The detector may be configured to detect the presence of fluid in contact with the membrane and/or in the fluid reservoir on the basis of a cross correlation of a curve of the detected values of the at least one electrical parameter as a function of the vibration frequency with two or more reference curves. In particular, one reference curve may represent characteristic values of the at least one electrical parameter for the case that fluid in contact with the membrane and/or in the fluid reservoir is present and another reference curve may represent characteristic values of the at least one electrical parameter for the case that no fluid in contact with the membrane and/or in the fluid reservoir is present.

The reference curve or curves may be stored in the detector, e.g. in a memory, such as RAM and/or flash, of the detector.

The detector may comprise a processor, such as a CPU, or the like which is configured to perform the cross correlation of the detected values of the at least one electrical parameter with the one or more reference curves.

The controller, the sensor and/or the detector may be configured to perform low pass filtering on the curve of the detected parameter values so as to eliminate high-frequency background noise in the measurements.

By using a cross correlation of a curve of the detected values of the at least one electrical parameter as a function of the vibration frequency with one or more reference curves, the presence of fluid in contact with the membrane and/or in the fluid reservoir can be detected in a particularly reliable and accurate manner. The occurrence of detection errors, e.g. a detection of the absence of fluid if fluid is present and a detection of the presence of fluid if no fluid is present, can be minimised, thus ensuring a high degree of detection accuracy. Further, the presence or absence of fluid in contact with the membrane and/or in the fluid reservoir can be immediately detected upon activation of the aerosol generator.

In one embodiment, the detector is configured to detect the presence of fluid in contact with the membrane and/or in the fluid reservoir on the basis of the slope or slopes, i.e. the gradient or gradients, of the curve of the detected values of the at least one electrical parameter as a function of or as dependent on the vibration frequency. For example, the slope or slopes of the curve may be determined between one or more of the detected values and the respective neighbouring or adjacent detected value or values. The slope or slopes may be determined for one or more regions of the curve or for the entire curve.

The detector may comprise a processor, such as a CPU, or the like which is configured to determine the slope or slopes of the curve of the detected values of the at least one electrical parameter as a function of the vibration frequency.

The controller, the sensor and/or the detector may be configured to perform low pass filtering on the curve of the detected parameter values so as to eliminate high-frequency background noise in the measurements.

It has been found that the curves of the detected values of the at least one electrical parameter as a function of the vibration frequency have more, narrower and/or higher peaks if no fluid is present in contact with the membrane and/or in the fluid reservoir. The presence of these peaks in the curve, indicating the absence of fluid in contact with the membrane and/or in the fluid reservoir, results in a corresponding change of the slopes of the curve of the detected values. Hence, based on the slope or slopes of this curve, the presence of fluid in contact with the membrane and/or in the fluid reservoir can be detected in a particularly simple and reliable manner. Further, the presence or absence of fluid in contact with the membrane and/or in the fluid reservoir can be immediately detected upon activation of the aerosol generator.

In one embodiment, the detector is configured to detect the presence of fluid in contact with the membrane and/or in the fluid reservoir on the basis of the length of the curve of the detected values of the at least one electrical parameter as a function of or dependent on the vibration frequency.

Herein, the term "length of the curve" is defined as the sum of the distances between neighbouring or adjacent detected values of the at least one electrical parameter. Thus, neighbouring or adjacent detected parameter values are connected with each other by straight lines and the lengths of these straight lines are summed up to obtain the length of the curve.

The detector may comprise a processor, such as a CPU, or the like which is configured to determine the length of the curve of the detected values of the at least one electrical parameter as a function of the vibration frequency.

The controller, the sensor and/or the detector may be configured to perform low pass filtering on the curve of the detected parameter values so as to eliminate high-frequency background noise in the measurements.

The presence of more, narrower and/or higher peaks in the curve of the detected parameter values in the case that no fluid in contact with the membrane and/or in the fluid reservoir is present results in an increased length of the curve. Hence, based on the length of the curve, the presence of fluid in contact with the membrane and/or in the fluid reservoir can be detected in a particularly reliable and simple manner. Further, the presence or absence of fluid in contact with the membrane and/or in the fluid reservoir can be immediately detected upon activation of the aerosol generator.

In one embodiment, the detector is configured to detect the presence of liquid in contact with the membrane and/or in the fluid reservoir on the basis of the difference obtained by subtracting a curve of the detected values of the at least one electrical parameter as a function of or dependent on the vibration frequency obtained in one detection cycle, e.g. a first detection cycle, from a curve of the detected values of the at least one electrical parameter as a function of or dependent on the vibration frequency obtained in another detection cycle, e.g. a second detection cycle. The difference may be obtained by subtracting the curves of two consecutive or successive detection cycles.

Herein, the term "detection cycle" defines a cycle of detection or measurement in which the at least one electrical parameter of the vibrator is detected, sensed or measured for each of the plurality of different vibration frequencies.

The detector may comprise a processor, such as a CPU, or the like which is configured to determine the difference between the two curves.

The controller, the sensor and/or the detector may be configured to perform low pass filtering on one or both of the curves of the detected parameter values so as to eliminate high-frequency background noise in the measurements.

By obtaining the difference between the curves of two detection cycles in this way, any changes in the curve induced by the absence of fluid or liquid in contact with the membrane and/or in the fluid reservoir can be reliably detected. Since the difference between the curves of two detection cycles is taken as the basis for fluid detection, any influence or effect of the structural details of the aerosol generator on the detection result is efficiently eliminated. Hence, in this way, the presence of fluid in contact with the membrane and/or in the fluid reservoir can be detected in a particularly accurate manner.

In one embodiment, the detector is configured to detect the presence of fluid in contact with the membrane and/or in the fluid reservoir on the basis of the area under the curve of the detected values of the at least one electrical parameter as a function of or dependent on the vibration frequency. The area under the curve may be the area between the curve and a straight line between the first detected parameter value and the last detected parameter value, i.e. between the first and last points of the curve.

The detector may comprise a processor, e.g. a CPU, or the like which is configured to determine or calculate the area under the curve.

The controller, the sensor and/or the detector may be configured to perform low pass filtering on the curve of the detected parameter values so as to eliminate high-frequency background noise in the measurements.

It has been found that the curve of the detected values of the at least one electrical parameter has peaks with larger amplitudes (higher peaks) if no fluid in contact with the membrane and/or in the fluid reservoir is present, resulting in an increased area under the curve. Thus, based on the area under the curve, the presence of fluid in contact with the membrane and/or in the fluid reservoir can be detected in a particularly reliable and simple manner. Further, the presence or absence of fluid in contact with the membrane and/or in the fluid reservoir can be immediately detected upon activation of the aerosol generator.

In one embodiment, the detector is configured to detect the presence of fluid in contact with the membrane and/or in the fluid reservoir on the basis of a Fourier transformation of the curve of the detected values of the at least one electrical parameter as a function of or dependent on the vibration frequency. By Fourier transformation, a function of frequency is transformed into a new time dependent function, i.e. a function whose argument is time, and vice versa.

The detector may comprise a processor, e.g. a CPU, or the like which is configured to calculate the Fourier transform of the curve of the detected parameter values.

The controller, the sensor and/or the detector may be configured to perform low pass filtering on the curve of the detected parameter values so as to eliminate high-frequency background noise in the measurements.

By Fourier transformation of the curve of the detected parameter values, the portions of the frequencies with short/long wavelength can be easily determined. For the case that no fluid in contact with the membrane and/or in the fluid reservoir is present, the Fourier transform of the curve of the detected parameter values has higher-frequency portions. Thus, based on the Fourier transform of the curve of the detected parameter values, the presence of fluid in contact with the membrane and/or in the fluid reservoir can be determined in a simple manner. Further, the presence or absence of fluid in contact with the membrane and/or in the fluid reservoir can be immediately detected upon activation of the aerosol generator.

The at least one electrical parameter may be the voltage and/or the current and/or the power and/or the current/voltage phase shift. For example, the at least one electrical parameter may be the current consumption, the current drain, the current draw or the like of the vibrator. The at least one electrical parameter may be the voltage drop or voltage consumption at the vibrator, e.g. at a piezoelectric element. The at least one electrical parameter may be the voltage applied to the vibrator, e.g. by the controller.

Each of these electrical parameters allows for a reliable and efficient detection of the presence of fluid in contact with the membrane and/or in the fluid reservoir. Moreover, these parameters can be detected, sensed or measured in a simple way, e.g. by using one or more current and/or voltage sensors, in a direct or in an indirect sensing method.

In one embodiment, the controller is configured to deactivate, e.g. automatically deactivate, the vibrator if no presence of fluid or liquid in contact with the membrane and/or in the fluid reservoir is detected by the detector. In this way, a user of the aerosol delivery device is provided with a clear indication that no fluid in contact with the membrane and/or in the fluid reservoir is present. Thus, the aerosol dosage accuracy is increased, thereby improving the efficiency of the aerosol treatment. Further, by deactivating the vibrator, the power consumption of the aerosol generator can be minimised, e.g., increasing the lifetime of a battery in the aerosol delivery device. This may also optimize the patient adherence and patient compliance.

In an embodiment of the invention, it is also possible to save the electronic parameter, curves, analyses and/or data in a memory e.g. of the CPU, such as mentioned in DE 102005006372 B4. In an embodiment of the invention, the electronic parameter, curves, analyses and/or data are transferred to a memory, smartphone, databank, electric cloud (I-Cloud), which may be located or owned by medical providers, hospitals, physicians, patients, clinical research centres, governmental databanks, and reimbursement cases, health insurances and/or pharmaceutical companies.

The controller may be configured to output a signal, such as a tactile signal, an audio signal, an optical signal, such as a flashlight, or the like, if no presence of fluid or liquid in contact with the membrane and/or in the fluid reservoir is detected by the detector. In this way, the user's attention is immediately drawn to the absence of fluid in contact with the membrane and/or in the fluid reservoir.

The aerosol delivery device may comprise a signal emitting means for emitting a signal, such as a tactile signal, an audio signal, an optical signal, such as a flashlight, or the like, indicating that no fluid in contact with the membrane and/or in the fluid reservoir is present. The signal emitting means may be electrically connected to the sensor, e.g. via a connecting line. The signal emitting means may be electrically connected to the controller or form part of the controller.

The controller may be configured to sequentially operate the vibrator at 40 or more, preferably 50 or more, more preferably 60 or more, even more preferably 70 or more and yet even more preferably 75 or more different vibration frequencies. By choosing a number of different vibration frequencies in this range, the presence of fluid in contact with the membrane and/or in the fluid reservoir can be detected with a particularly high degree of accuracy.

The controller may be configured to switch the vibrator from one vibration frequency (f1) to the next vibration frequency (f2) within a time period of 20 ms or less, preferably 18 ms or less, more preferably 16 ms or less, even more preferably 15 ms or less and yet even more preferably 14 ms or less. In this way, the time period required for detecting the presence of fluid in contact with the membrane and/or in the fluid reservoir can be kept low, so that any influence of the detection process on aerosol delivery can be particularly reliably prevented.

Preferably, the detection process has a duration of less than 1 s, more preferably less than 900 ms, even more preferably less than 800 ms, yet even more preferably less than 700 ms and still yet even more preferably less than 600 ms.

The controller may be configured to sequentially operate the vibrator at a plurality of different vibration frequencies in the range of 30 to 60 kHz and/or 90 to 170 kHz and/or 350 to 600 kHz. These vibration frequency ranges were found to allow for a particularly reliable and efficient detection of the presence of fluid in contact with the membrane and/or in the fluid reservoir.

The controller may be configured to sequentially operate the vibrator at a plurality of different vibration frequencies so that the difference between one vibration frequency (f1) and the next vibration frequency (f2) is not more than 5% of the one vibration frequency (f1), preferably not more than 3% of the one vibration frequency (f1), more preferably not more than 2% of the one vibration frequency (f1) and even more preferably not more than 1% of the one vibration frequency (f1). In this way, it can be particularly reliably ensured that also very narrow peaks, e.g. very narrow resonance peaks, in the curve of the detected parameter values are identified, thus further increasing the accuracy of the detection process.

The controller may be configured to sequentially operate the vibrator at a plurality of different vibration frequencies so that the difference between one vibration frequency (f1) and the next (f2), i.e. adjacent or neighbouring, vibration frequency is constant for all the vibration frequencies or, alternatively, the vibration frequency is a function, e.g. an ongoing or continuous function, of the vibration frequencies, e.g. delta f ($\Delta f$)~1/f, or alternatively a function of f1 and/or f2. Hence, the vibration frequencies may be equidistantly spaced. In this way, the entire frequency range can be uniformly analysed or investigated, thus further increasing the detection accuracy.

The membrane of the aerosol generator may be a passive membrane. The vibrator may be configured to vibrate a fluid supply system and/or a membrane back space of the aerosol delivery device.

The membrane of the aerosol generator may be an active membrane, e.g. a vibratable or oscillatable membrane. The vibrator may be configured to vibrate the membrane.

The invention further provides a method of operating an aerosol delivery device. The aerosol delivery device comprises an aerosol generator for generating an aerosol in the aerosol delivery device with a membrane, e.g. a vibratable membrane, and a vibrator configured to vibrate a fluid and to aerosolise the fluid by the membrane. The aerosol delivery device further comprises a fluid or liquid reservoir for receiving the fluid or liquid to be aerosolised, the fluid or liquid reservoir being arranged in fluid communication with the vibratable membrane.

The method comprises the steps of sequentially operating the vibrator at a plurality of different vibration frequencies, detecting, sensing or measuring at least one electrical parameter of the vibrator for each of the plurality of different vibration frequencies, and detecting or determining the presence of fluid or liquid in contact with the membrane and/or in the fluid reservoir on the basis of the dependence of the detected values of the at least one electrical parameter on the vibration frequency.

The method of the invention provides the advantageous effects already described in detail above for the device of the invention. In particular, the method enables a reliable and efficient detection of the presence of fluid in contact with the membrane and/or in the fluid reservoir.

The step of sequentially operating the vibrator at a plurality of different vibration frequencies may be performed by using a controller, such as the controller described above. The step of detecting at least one electrical parameter of the vibrator for each of the plurality of different vibration frequencies may be performed by using a sensor, such as the sensor described above. The step of detecting the presence of fluid in contact with the membrane and/or in the fluid reservoir on the basis of the dependence of the detected values of the at least one electrical parameter on the vibration frequency may be performed by using a detector, such as the detector described above.

The presence of fluid in contact with the membrane and/or in the fluid reservoir may be detected on the basis of a cross correlation of a curve of the detected values of the at least one electrical parameter as a function of the vibration frequency with a reference curve. The reference curve may be formed as a production median value or in a simplified manner (simplified curve).

The presence of fluid in contact with the membrane and/or in the fluid reservoir may be detected on the basis of the slope or slopes, i.e. the gradient or gradients, of the curve of the detected values of the at least one electrical parameter as a function of the vibration frequency.

The presence of fluid in contact with the membrane and/or in the fluid reservoir may be detected on the basis of the length of the curve of the detected values of the at least one electrical parameter as a function of the vibration frequency.

The presence of fluid in contact with the membrane and/or in the fluid reservoir may be detected on the basis of the difference obtained by subtracting a curve of the detected values of the at least one electrical parameter as a function of the vibration frequency obtained in one detection cycle from a curve of the detected values of the at least one electrical parameter as a function of the vibration frequency obtained in another detection cycle.

The presence of fluid in contact with the membrane and/or in the fluid reservoir may be detected on the basis of the area under the curve of the detected values of the at least one electrical parameter as a function of the vibration frequency.

The presence of fluid in contact with the membrane and/or in the fluid reservoir may be detected on the basis of a Fourier transformation or transform of the curve of the detected values of the at least one electrical parameter as a function of the vibration frequency.

The at least one electrical parameter may be the voltage and/or the current and/or the power and/or the current/voltage phase shift.

The method may further comprise the step of deactivating, e.g. automatically deactivating, the vibrator if no presence of fluid in contact with the membrane and/or in the fluid reservoir is detected.

The method may further comprise the step of outputting a signal, such as a tactile signal, an audio signal, an optical signal, such as a flashlight, or the like, if no presence of fluid in contact with the membrane and/or in the fluid reservoir is detected.

The vibrator may be sequentially operated at 40 or more, preferably 50 or more, more preferably 60 or more, even more preferably 70 or more and yet even more preferably 75 or more different vibration frequencies.

The vibrator may be switched from one vibration frequency to the next vibration frequency within a time period of 20 ms or less, preferably 18 ms or less, more preferably 16 ms or less, even more preferably 15 ms or less and yet even more preferably 14 ms or less.

The vibrator may be sequentially operated at a plurality of different vibration frequencies in the range of 30 to 60 kHz and/or 90 to 170 kHz and/or 350 to 600 kHz.

The vibrator may be sequentially operated at a plurality of different vibration frequencies so that the difference between one vibration frequency and the next vibration frequency is not more than 5% of the one vibration frequency, preferably not more than 3% of the one vibration frequency, more preferably not more than 2% of the one vibration frequency and even more preferably not more than 1% of the one vibration frequency.

The vibrator may be sequentially operated at a plurality of different vibration frequencies so that the difference between one vibration frequency and the next vibration frequency is constant for all the vibration frequencies or, alternatively, the vibration frequency is a function, e.g. an ongoing or continuous function, of the vibration frequencies, e.g. delta f $(\Delta f) \sim 1/f$, or alternatively a function of f1 and/or f2. Hence, the vibration frequencies may be equidistantly spaced. In this way, the entire frequency range can be uniformly analysed or investigated, thus further increasing the detection accuracy.

The membrane of the aerosol generator may be a passive membrane. The vibrator may be configured to vibrate a fluid supply system and/or a membrane back space of the aerosol delivery device.

The membrane of the aerosol generator may be an active membrane, e.g. a vibratable or oscillatable membrane. The vibrator may be configured to vibrate the membrane.

The method of the invention is a method of operating the aerosol delivery device of the invention. Hence, the further features disclosed in connection with the above description of the device of the invention may also be applied to the method of the invention.

The aerosol delivery device of the invention may comprise the fluid, i.e. the fluid to be aerosolised.

The fluid to be aerosolised may contain one or more active agents. The one or more active agents may be selected from the group consisting of an anti-epileptic drug, an anti-convulsive drug, an anti-emetic, a immunemodulator, a pain killer, an anti-rheumatic, an anti-cancer drug, a mucolytic drug, a sleeping assistant, an anti-mycotic, a sexual stimulant, a protein or peptide, heparane and a gene, and/or the group consisting of an anti-diabetic drug, insulin and a hormone, and/or the group consisting of a corticosteroid, a leukotriene antagonist, a bradykinin antagonist, a cromone, an anti-histamine and an antibody, and/or the group consisting of an aminoglycoside, a cephalosporine, a macrolide, a chonolone, a nitroimidazol, a glycopeptide, a polyen-antibiotic, a beta-lactam, a tetracycline, a quinolone, a sulfonamide, and an azol derivative, and/or the group consisting of a benzodiazepine, a barbitute and a succinimide, and/or the group consisting of alpha antitrypsine, erythropoetine, interferones, kinases, elastases, peptides and proteines, and/or the group consisting of salbutamol, levalbuterol, formoterol, fenoterol, salmeterol, bambuterol, brocaterol, clenbuterol, terbutalin, tulobuterol, epinephrin, isoprenalin, and hexoprenalin, and/or the group consisting of tiotropium, oxitropium, ipratropium, and glcopyrrolate, and/or the group consisting of acetylcystein, ambroxol, carbocystein, tyloxapol, dipalmytoylphosphatidylcholin, recombinant surfactant proteins, and D-Nase, and/or the group consisting of surfactants, and/or the group consisting of cromoglycate, nedocromil, beclomethasone, betamethasone, budesonide, ciclesonide, flunisolide, fluticasone, icomethasone, mometasone, rofleponide, triamcinolone, bradykinine-, prostaglandine-, leucotriene- and platelet activating factor antagonists, and/or the group consisting of amoxycillan, piperacillin, clavulan acid, sulbactam, cefaclor, cefazedon, Cefuroxim, Cefoxitin, cefodizim, cefsulodin, cefpodixim, cefixim, colistin, imipenem, cilastatin, az-trenonam, streptomycin, neomycin, paromomycin, kanamycin, gentamycin, amicacin, tobramycin, spectinomycine, doxycyclin, minocycline, erythromycine, clarithromycine, roxithromycine, azithromycine, josamycine, spiramycine, Ciprofloxacin, Ofloxacine, Levofloxacine, pefloxacine, lomefloxacine, fleroxacine, clinafloxacine, sitafloxacine, gemifloxacine, balofloxacine, trovafloxacine, moxifloxacine, metronidazol, tinidazol, chloramphenicol, lincomycine, clindamycine, fosfomycine, vancomycine and teicoplanine, and/or the group consisting of refampicine, isoniacide, cycloserine, terizidone, and ansamycine, and/or the group consisting of clotrimazol, oxiconazol, miconazol, ketoconazol, itraconazol, fluconazol, amphotericine B, natamycine, nystatine, flucytosine, and Pentamidine, and/or the group consisting of dimepranol-4-acetate amideo benzoate, thymopentin, interfer-ones, filgrastine, interleukine, azathioprine, and cyclosporine; virustatics such as podophyllotoxine, vidarabine, tromantadine, zidovudine, and a-antitrypsin, and/or the group consisting of corticotro-pine, tetracosactide, choriogonandotropine, urofolitropine, urogonadotropine, saomatotropine, metergoline, desmopressine, oxytocine, argipressine, or-nipressine, leuproreline, triptoreline, gonadoreline, busereline, nafareline, goselerine, somatostatine, parathyroide gland hormones, Dihydrotachysterole, calcitonine, clodron acid, etidron acid, thyroid gland therapeutics, anabolics, androgens, etrogens, gestagenes, and antiestrogenes, and/or the group consisting of nimustine, melphanlane, carmustine, lomustine, cyclophosphosphamide, ifosfamide, trofosfamide, chlorambucil, busulfane, treosulfane, prednismustine, thiotepa, cytarabine, fluorouracil, mercaptopurine, tioguanine, vinblastine, vincristine, vindesine, alcarubicine, bleomycine, dactinomycine, daunorubicine, doxorubicine, epirubicine, idarubicine, mitomycine, plicamycine, carboplatinum, cis-platinum, titanocendichloride Amsacrine, dacarbazine, estramustine, etoposide, hydroxycarbamide, mitoxanthrone, procarbazine, and temiposide, and/or the group consisting of Proxibarbal, lisuride, methysergide, dihydroergotamine, ergotamine, clonidine, pizotifene, bezodiazepines, barbiturates, cyclopyrrolones, imidazopyridines, arbiturates, Pheytoin, Primidone, mesuximide, ethosuximide, sultiam, carbamezepin, valproic acid, vigabatrine, Levodopa, carbidopa, benserazide, selegiline, bromocriptine, amantadine, tiapride, Thiethylperazine, bromopride, domperidone, granisetrone, ondasetrone, tropisetrone, pyridoxine, morphine, codeine, hydromorphone, methadone, fenpipramide, fentanyl, piritramide, pentazocine, buprenorphine, nalbuphine, tilidine, N-methylated barbiturates, thiobarbiturates, ketamine, etomidate, propofol, benzodiazepines, droperidol, haloperidol, alfentanyl, sulfentanyl, tumor necrosis factor alpha and non-steroidal anti-inflammatory drugs, and/or the group consisting of insulin, sulfonylurea derivatives, biguanids, glitizols, glucagon, diazoxid, interleukines, interferones, tumor necrosisfactor (TNF), and colony stimulating factors, and/or the group consisting of proteins, peptides, heparine, heparinoids, urokinases, streptokinases, ATP-ase, prostacycline, sexual stimulants, and genes.

By using the aerosol delivery device and/or method of the invention to aerosolise fluids containing one or more of the above active agents and to deliver the resulting aerosols, e.g. through the respiratory tract, for example by the nasal or pulmonary route, the activity or effectiveness of the one or more active agents at a desired location can be enhanced, thereby ensuring a particularly efficient aerosol treatment.

BRIEF DESCRIPTION OF THE DRAWINGS

Hereinafter, non-limiting examples of the invention are explained with reference to the drawings, in which:

FIG. 2 shows diagrams of the voltage of the vibrator of the aerosol delivery device shown in FIG. 1 as a function of the vibration frequency, wherein FIG. 2(a) shows two reference curves, one with fluid and the other without fluid, and FIG. 2(b) shows two measured curves of the detected values of the voltage, one with fluid and the other without fluid;

FIG. 7 shows diagrams illustrating a Fourier transformation, wherein FIG. 7(a) shows the voltage of the vibrator of the aerosol delivery device shown in FIG. 1 as a function of the vibration frequency, presenting two curves of the detected voltage values, one with fluid and the other without fluid, and FIG. 7(b) shows the Fourier transforms of the two curves shown in FIG. 7(a).

DETAILED DESCRIPTION OF CURRENTLY PREFERRED EMBODIMENTS

Figure 1:
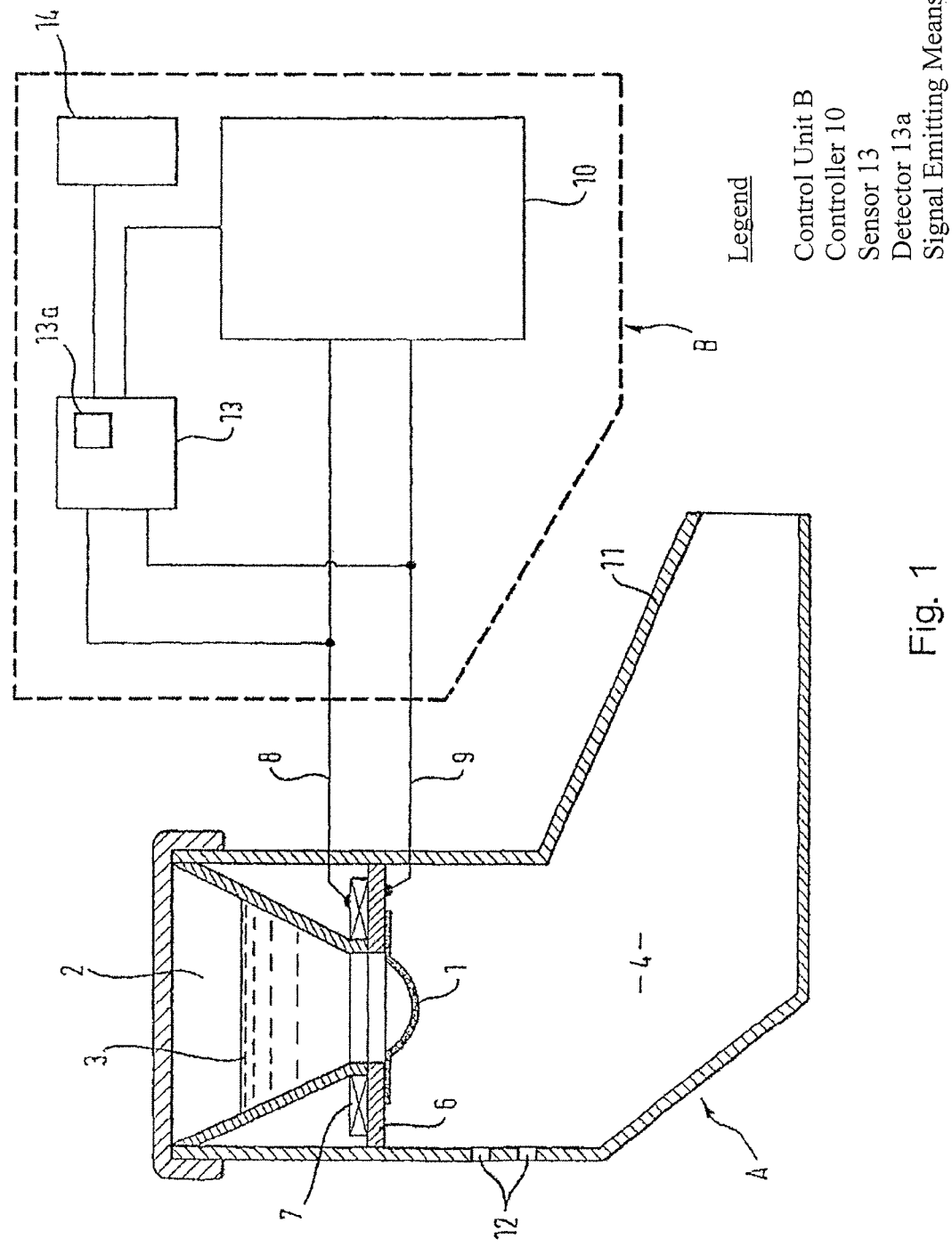
FIG. 1 shows a schematic longitudinally cut cross-sectional view of an aerosol delivery device according to an embodiment of the present invention.

FIG. 1 shows a schematic longitudinally cut cross-sectional view of an aerosol delivery device A according to a currently preferred embodiment of the present invention.

The aerosol delivery device A comprises an aerosol generator consisting of a vibratable membrane 1, a support unit 6 and a vibrator 7, e.g., an electromechanical transducer unit, such as a piezo-element, which is configured to vibrate the membrane 1. The membrane 1 is attached to the support unit 6 which supports the membrane 1 and to which the vibrator 7 is also attached. The aerosol delivery device A further comprises a fluid reservoir 2 for receiving a fluid 3 to be aerosolised, the fluid reservoir 2 being arranged in fluid communication with the membrane 1, and a controller 10 which is configured to sequentially operate the vibrator 7 at a plurality of different vibration frequencies.

Moreover, the aerosol delivery device A comprises a sensor 13 which is configured to detect, sense or measure at least one electrical parameter of the vibrator 7 for each of the plurality of different vibration frequencies and a detector 13a which is configured to detect or determine the presence of fluid 3 in contact with the membrane 1 on the basis of the dependence of the detected values of the at least one electrical parameter on the vibration frequency.

The controller 10 is electrically connected to the vibrator 7 via connecting lines 8, 9. The sensor 13 is connected to the connecting lines 8, 9 and to the controller 10 via separate connecting lines. Further, the aerosol delivery device A comprises a signal emitting means 14 for emitting a signal, such as a tactile signal, an audio signal, an optical signal or the like, indicating that no fluid in contact with the membrane 1 is present. The signal emitting means 14 is electrically connected to the sensor 13 via a connecting line. Alternatively, the signal emitting means 14 may be electrically connected to the controller 10.

The membrane 1, the support unit 6 and the vibrator 7 are configured in a rotationally symmetrical manner in the embodiment described here and together form a vibratable or oscillatable structure.

The controller 10, the sensor 13, the detector 13a and the signal emitting means 14 are accommodated together in a control unit B. The detector 13a is integrated with the sensor 13, i.e., the sensor 13 and the detector 13a are provided as a combined unit.

The aerosol delivery device A further comprises a mixing chamber or aerosol cavity 4 in fluid communication with the membrane 1. The mixing chamber or aerosol cavity 4 is arranged on the side of the membrane 1 which is opposite to the membrane side facing the fluid reservoir 2. One or more air holes 12 are provided in the housing of the aerosol delivery device A. A mouthpiece or nosepiece 11 of the aerosol delivery device A is provided in fluid communication with the mixing chamber or aerosol cavity 4.

The mixing chamber or aerosol cavity 4 may contain e.g. one or more inhalation valves and one or more exhalation valves (not shown). The aerosol generator may produce an aerosol cloud in the mixing chamber or aerosol cavity 4 during the exhalation phase, when the air (fluid) passes through the exhalation valve(s), and accumulate a high aerosol amount in the mixing chamber or aerosol cavity 4 for the next inhalation phase. In this case, the aerosol delivery device works like a breath enhanced device, similar to an aerosol bolus, such as e.g. mentioned in DE 19953317, EP 1227856, DE 102008054431 or EP 2361108.

In the following, an example of the operation of the aerosol delivery device A shown in FIG. 1, exemplifying an embodiment of the method of the invention, will be explained.

An activation signal of the controller 10 is supplied to the vibrator 7 via the connecting lines 8, 9, causing the membrane 1 to vibrate. The fluid 3, e.g., a liquid, stored in the fluid reservoir 2 and abutting the membrane 1 is conveyed through holes or openings (not shown) in the vibrating membrane 1 and thereby aerosolised into the aerosol mixing chamber 4. The aerosol thus provided in the aerosol mixing chamber 4 can be inhaled by a user or patient through the mouthpiece or nosepiece 11 of the aerosol delivery device A. In order to supply a sufficient amount of air, ambient air can enter through the one or more air holes 12 into the aerosol mixing chamber 4 during inhalation. Further, the air exhaled by the patient or user can exit from the aerosol mixing chamber 4 through the one or more air holes 12 during exhalation.

Different electrical properties of the vibratable or oscillatable structure 1, 6, 7, such as the voltage, the current, the power and/or the current/voltage phase shift, are dependent, in particular, on the capacity of the vibrator 7. The vibratable or oscillatable structure 1, 6, 7, in particular, the vibrator 7, display very specific characteristics during aerosolisation and during operation without liquid, which are reflected in the electrical parameters of the vibrator 7. The operating stage with and without fluid on the membrane 1 can thus be reliably determined by means of these electrical parameters.

In order to detect at least one electrical parameter of the vibrator 7, the sensor 13 is connected to the vibrator 7 via the connecting lines 8, 9 and/or the controller 10. In this way, the at least one electrical parameter of the vibrator 7 is supplied to the sensor 13. For example, the connecting lines 8, 9 may be configured such that during operation of the controller 10 at least one electrical parameter of the vibrator 7 is transmitted to the sensor 13 via the connecting lines 8, 9 and can be detected thereby. Detection of the at least one electrical parameter of the vibrator 7 by the sensor 13 can occur continuously or at discrete time intervals, as has been detailed above.

The controller 10 sequentially operates the vibrator 7 at a plurality of different vibration frequencies, e.g. 80 different, distantly spaced vibration frequencies in the frequency range of 30 to 60 kHz, and the sensor 13 detects, senses or measures at least one electrical parameter, such as the voltage, of the vibrator 7 for each of these different vibration frequencies. The detector 13a which, in the present embodiment, is integrally formed with the sensor 13 analyses the dependence of the values of the at least one electrical parameter detected by the sensor 13 on the vibration frequency and detects or determines the presence of fluid 3 in contact with the membrane 1 on the basis of this dependence. The details of this detection process will be discussed in detail below with reference to FIGS. 2 to 7 for various embodiments of the present invention.

If the detector 13a determines that there is no fluid 3 in contact with the membrane 1, i.e. no more fluid 3 stored in the fluid reservoir 2, the detector 13a may emit a signal to the controller 10, which in turn automatically stops the supply of activation signals to the vibrator 7, thereby automatically switching off the aerosol delivery device A. Alternatively or additionally, the detector 13a may instruct the signal emitting means 14 to emit a signal, such as a tactile signal, an audio signal, an optical signal or the like, to indicate to the patient or user that the aerosol delivery device A has consumed the fluid 3 stored in the fluid reservoir 2, which signals the end of the aerosol therapy session to the patient or user. In this case, the patient or user may then switch off the aerosol delivery device A if no automatic switch off function is provided in addition to the signal output. For example, an audio signal emitted for this purpose may be a short sound signal of 0.5 to 2 seconds in length. In an embodiment of the invention e.g. a monitor system may be included to measure the patient adherence and use therefore the data. The data may therefore be measured, evaluated, analysed, stored and/or transferred. The data may be results for e.g. electrical parameters, curves, analyses and/or data.

Figure 2:
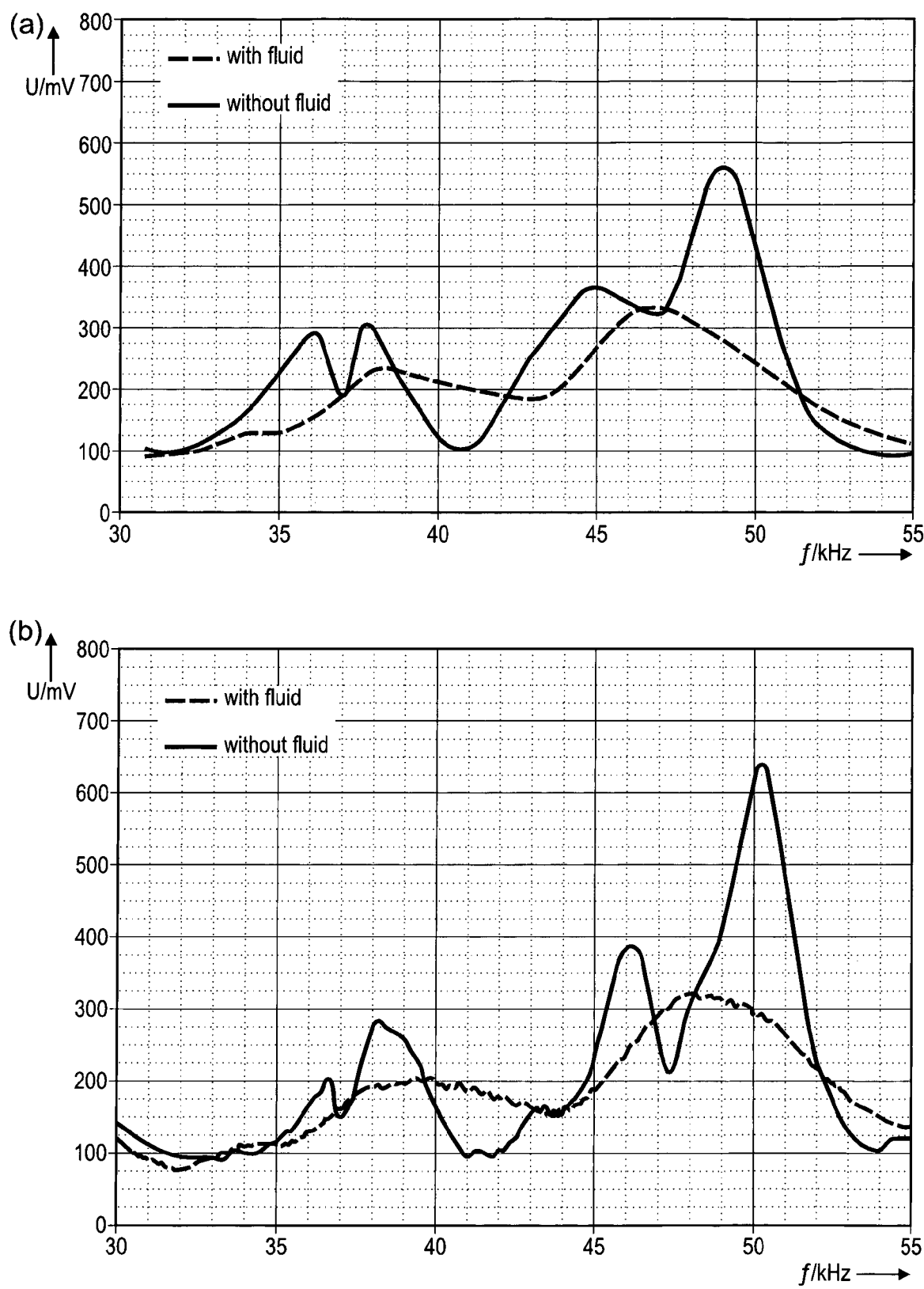

FIG. 2 illustrates an embodiment of the present invention in which the presence of fluid 3 in contact with the membrane 1 is detected by the detector 13a on the basis of a cross correlation of a curve of the detected values of the at least one electrical parameter as a function of the vibration frequency with a reference curve.

In this embodiment, the at least one electrical parameter is the voltage of the vibrator 7, i.e. the voltage applied to the vibrator 7 by the controller 10. However, the present invention is not limited thereto.

FIG. 2(*a*) shows two reference curves of the voltage of the vibrator 7 as a function of the vibration frequency in the range from 30 to 55 kHz to be used for the cross correlation, wherein one curve was obtained with fluid in contact with the membrane 1 and the other curve was obtained without fluid in contact with the membrane 1. Both reference curves were obtained by performing 80 detections or measurements of the voltage of the vibrator 7 as dependent on the vibration frequency in the frequency range from 30 to 55 kHz under constant conditions and by forming the mean voltage values for each vibration frequency from these 80 measurements or detections. Alternatively, both reference curves may use e.g. from 20 up to 250 detections or measurements of the electrical parameter. In a further alternative, both reference curves may use e.g. from 45 up to 125 detections or measurements of the electrical parameter.

The reference curves are stored in the detector 13a, e.g., in a memory, such as RAM and/or flash. The reference curves may also be transferred, received or sent from or to a transportable memory, smartphone, databank electric cloud (I-Cloud) and/or the like.

FIG. 2(*b*) shows two curves of voltage values of the vibrator 7 detected by the sensor 13 for the different vibration frequencies applied to the vibrator 7 by the controller 10. One of these two curves was measured with fluid 3 in contact with the membrane 1 and the other of these curves was measured without fluid 3 in contact with the membrane 1.

The detector 13a is configured to detect the presence of fluid 3 in contact with the membrane 1 on the basis of a cross correlation of the curve of the detected values of the voltage of the vibrator 7 as a function of the vibration frequency with one or both of the two reference curves shown in FIG. 2(*a*). For example, if one of the two curves shown in FIG. 2(*b*) is detected or measured by the sensor 13, the detector 13a will perform a cross correlation of this curve with one or both of the reference curves of FIG. 2(*a*). Specifically, the detector 13a comprises a processor (not shown), such as a CPU or the like, configured to perform this cross correlation. The analyses (e.g. cross correlation) may be performed with the processor in the controller (or CPU), directly or indirectly via a computer, laptop, tablet, smartphone, PDA, flash, databank and/or cloud (I-Cloud).

As has been detailed above, the cross correlation provides a measure of the similarity of two curves. Hence, on the basis of a correlation coefficient obtained in the cross correlation, it can be detected or determined whether the measured voltage curve corresponds to the reference curve with fluid 3 or the reference curve without fluid 3. In this way, the presence of fluid 3 in contact with the membrane 1 can be reliably and efficiently determined.

The presence of fluid 3 in contact with the membrane 1 can be particularly accurately detected, if the detected or measured voltage curve is cross correlated with the reference curve with fluid 3 and the reference curve without fluid 3. In this case, the probabilities of both possible types of detection errors, i.e., a detection of the absence of fluid 3 in contact with the membrane 1 if fluid 3 is present (first type of error) and a detection of the presence of fluid 3 in contact with the membrane 1 if no fluid 3 is present (second type of error), were found to be less than 1%. With these analyses, also detection errors could be found to be less than 0.5% or even less than 0.1%. Hence, the vibrator 7 can be reliably deactivated if no fluid 3 in contact with the membrane 1 is present, while an undesired deactivation of the vibrator 7 in the case that fluid 3 in contact with the membrane 1 is present is securely prevented.

Figure 3:
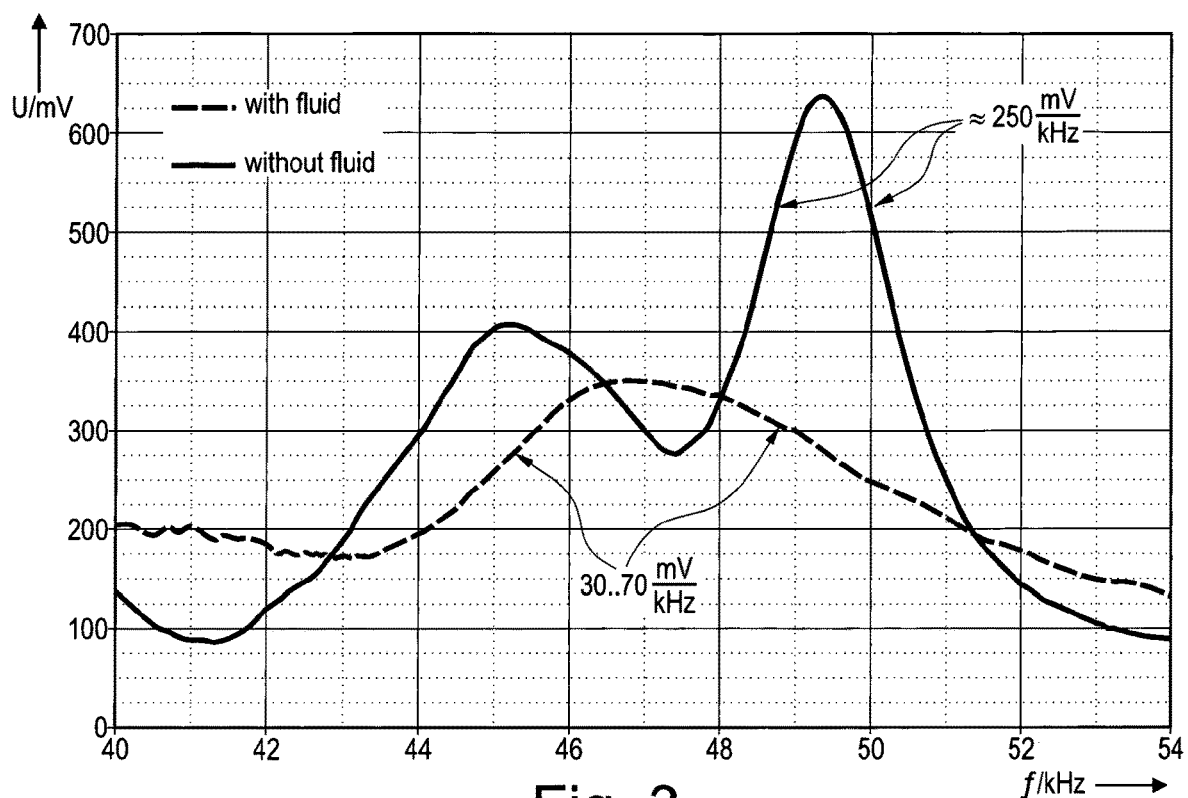
FIG. 3 shows a diagram of the voltage of the vibrator of the aerosol delivery device shown in FIG. 1, presenting two curves of the detected voltage values, one with fluid and the other without fluid.

FIG. 3 illustrates another embodiment of the present invention in which the presence of fluid 3 in contact with the membrane 1 is detected on the basis of the slopes of a curve of the detected values of the at least one electrical parameter of the vibrator 7 as a function of the vibration frequency. In this embodiment, the at least one electrical parameter is the voltage of the vibrator 7. However, the present invention is not limited thereto.

FIG. 3 shows two measured voltage curves in the frequency range from 40 to 54 kHz, one taken with fluid 3 in contact with the membrane 1 and the other taken without fluid 3 in contact with the membrane 1.

As can be seen from FIG. 3, these two curves differ significantly in the shapes of their peaks. In particular, the peaks of the curve without fluid 3 are considerably narrower and have a larger amplitude than those of the curve with fluid 3. Therefore, the curve without fluid 3 exhibits significantly larger slopes, in particular, larger maximum slopes. Specifically, in the example shown in FIG. 3, the absolute values of the maximum slopes of the curve taken with fluid 3 lie in the range from 30 to 70 mV/kHz, while the absolute value of the maximum slopes of the curve taken without fluid 3 is approximately 250 mV/kHz, as is indicated in the figure. Hence, the slope or slopes of the measured curve provide a reliable indication of the presence of fluid 3 in the contact with the membrane 1.

The detector 13a comprises a processor (not shown), such as a CPU or the like, configured to determine or calculate the slope or slopes of a measured curve of the at least one electrical parameter, i.e. the voltage in the present embodiment. The detector 13a, e.g. the processor thereof, is further configured to compare the slope or slopes, e.g. the maximum slope or slopes, thus determined with one or more reference values stored in the detector 13a, e.g., in a memory. Based on this comparison, the detector 13a detects or determines the presence of fluid 3 in contact with the membrane 1. The one or more slope reference values may be empirically determined or may be based on previous measurements, with and/or without fluid 3, or on mean slope values obtained by averaging a plurality of such previous measurements.

In this embodiment, the presence of fluid 3 in contact with the membrane 1 can be detected in a particularly simple manner. Further, the probability of an error of the first type was found to be less than 1% and the probability of an error of the second type was found to be only approximately 2%. Hence, this approach also provides a high degree of detection accuracy.

In a further embodiment, also a probability of an error of the first type may be acceptable with less than 2% or even with less than 3%, but this results in a lower degree of detection accuracy. In an alternative embodiment, also a probability of an error could be realised to be less than 0.5% or even less than 0.1%.

Figure 4:
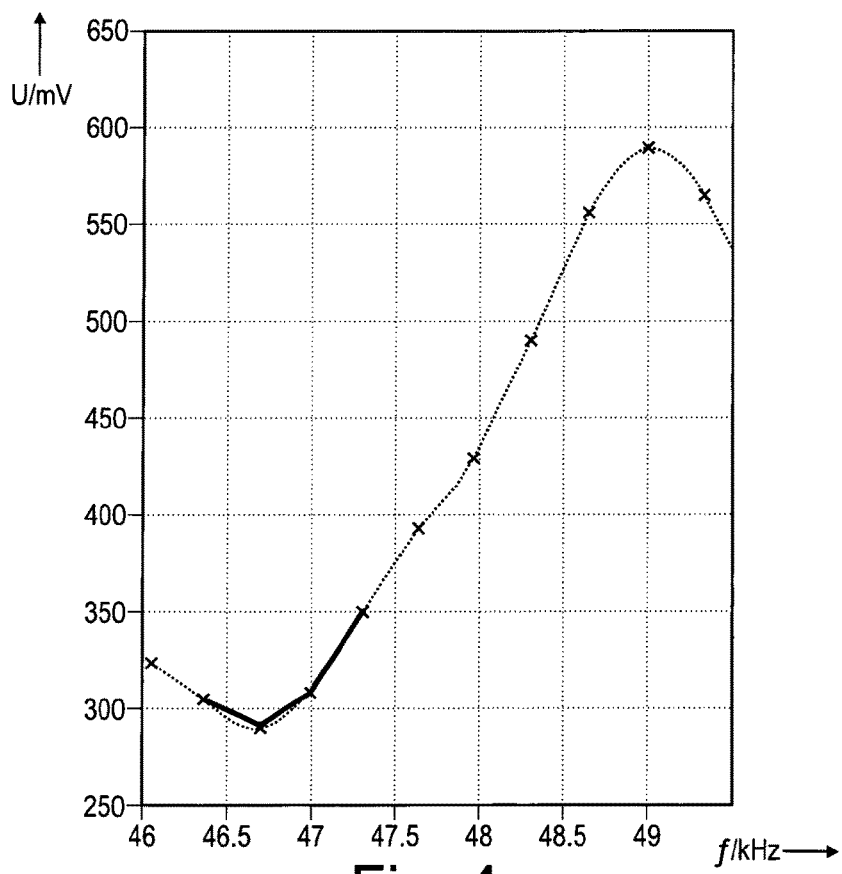
FIG. 4 shows a diagram of the voltage of the vibrator of the aerosol delivery device shown in FIG. 1 as a function of the vibration frequency without fluid.

FIG. 4 illustrates an embodiment of the present invention in which the length of the curve of the detected values of the at least one electrical parameter of the vibrator 7 as a function of the vibration frequency is used to detect the presence of fluid 3 in contact with the membrane 1. In this embodiment, the at least one electrical parameter is the voltage of the vibrator 7. However, the present invention is not limited thereto.

FIG. 4 shows a curve of the detected voltage values dependent on the vibration frequency in the frequency range of 46 to 49 kHz with fluid 3 in contact with the membrane 1.

As is indicated in FIG. 4 by three straight lines connecting the second to fifth detected or measured points of the curve, the length of the curve is determined by adding the distances between neighbouring or adjacent measurement points to each other, i.e., by summing up the straight connection lines between neighbouring or adjacent measurement points. The length of the curve thus obtained is compared with one or more reference values for the curve length which are stored in the detector 13a, e.g., in a memory thereof.

Specifically, the processor of the detector 13a, such as e.g. a separate processor, controller, CPU, smartphone, tablet, laptop, computer, databank, cloud or the like, is configured to determine the length of the measured curve. The comparison of the curve length thus obtained with the one or more reference values is also performed by this processor. This could be done as well in a simplified manner (simplified curve).

The one or more reference length values may be taken from previous measurements, e.g. by averaging a plurality of measurements, or may be empirically determined. The one or more reference values may be obtained for the case that fluid 3 in contact with the membrane 1 is present and/or for the case that no fluid 3 in contact with the membrane 1 is present.

For example, a first reference length value may be obtained for the case that fluid 3 in contact with the membrane 1 is present and a second reference length value may be obtained for the case that no fluid 3 in contact with the membrane 1 is present and the length of the curve of the detected voltage values may be compared with both of these reference length values.

On the basis of a comparison between the measured curve length and the one or more reference length values, the presence of fluid 3 in contact with the membrane 1 can be detected or determined in a reliable and efficient manner. It was found that the probabilities of the detection errors of the first and second types are less than 1%. Therefore, the presence of fluid 3 in contact with the membrane 1 can be detected or determined with a high degree of accuracy.

In an alternative embodiment, detection errors of the first and second types are less than 3% or less than 2%. In a further embodiment, the detection errors of the first and second types are less than 0.5 or even less than 0.1%.

Figure 5:
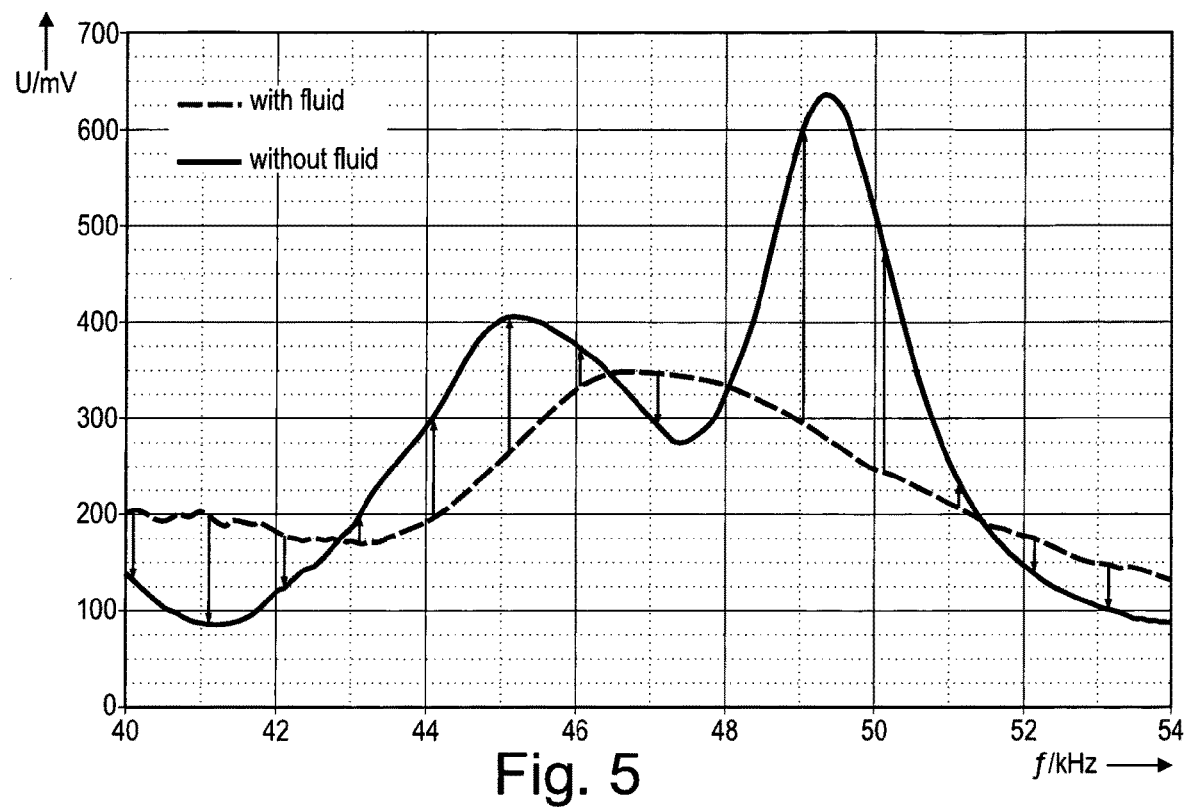
FIG. 5 shows a diagram of the voltage of the vibrator of the aerosol delivery device shown in FIG. 1, presenting two curves of the detected voltage values, one with fluid and the other without fluid, and indicating the difference between the two curves.

FIG. 5 illustrates an embodiment of the present invention in which the presence of fluid 3 in contact with the membrane 1 is detected on the basis of the difference obtained by subtracting a first curve of the detected values of the at least one electrical parameter of the vibrator 7 as a function of the vibration frequency obtained in a first detection cycle from a second curve of the detected values of the at least one electrical parameter of the vibrator 7 as a function of the vibration frequency obtained in a second detection cycle. In this embodiment, the at least one electrical parameter is the voltage of the vibrator 7. However, the present invention is not limited thereto.

In FIG. 5, such first and second measured voltage curves, obtained in a first and a second detection cycle, respectively, are shown, wherein the first curve was taken with fluid 3 in contact with the membrane 1 and the second curve was taken without fluid 3 in contact with the membrane 1.

As is schematically indicated by the plurality of vertical arrows in FIG. 5, the detector 13a subtracts the first measured voltage curve from the second measured voltage curve over the entire frequency range of 40 to 54 kHz. This subtraction process is performed by the processor, such as a CPU or the like, which is part of the detector 13a.

Alternatively, the detector 13a subtracts the first measured voltage curve from the second measured voltage curve over the entire frequency range of 10 to 200 kHz or in a range of 20 to 100 kHz.

In this way, a differential curve is obtained which provides the differences between the detected voltage values of the first and second detection cycles for each vibration frequency.

The differences between the detected voltage values of the first and second detection cycles thus obtained are compared with one or more reference values which are stored in the detector 13*a*, e.g. in a memory thereof. This comparison may be performed for some or all of the different vibration frequencies. The comparison is also performed by the processor of the detector 13*a*.

The one or more reference values may be obtained on the basis of previous measurements, e.g. reference measurements, for example, by performing one reference measurement with fluid 3 in contact with the membrane 1 and another reference measurement without fluid 3 in contact with the membrane 1 and subtracting the two curves from each other. Further, a plurality of such differences may be averaged or a plurality of reference measurements with and without fluid 3 in contact with the membrane 1 may each be averaged first and the averaged reference curves with and without fluid 3 may be subsequently subtracted from each other. Alternatively, the one or more reference values may be empirically determined.

Based on the comparison of the determined differences between the first and second measured voltage curves with the one or more reference values, the presence of fluid 3 in contact with the membrane 1 can be detected or determined in a reliable and efficient manner. It was found that the probabilities of the detection errors of the first and second type are less than 1%. Alternatively, also detection errors of the first and second type of less than 0.5% or even less than 0.1% are possible.

Figure 6:
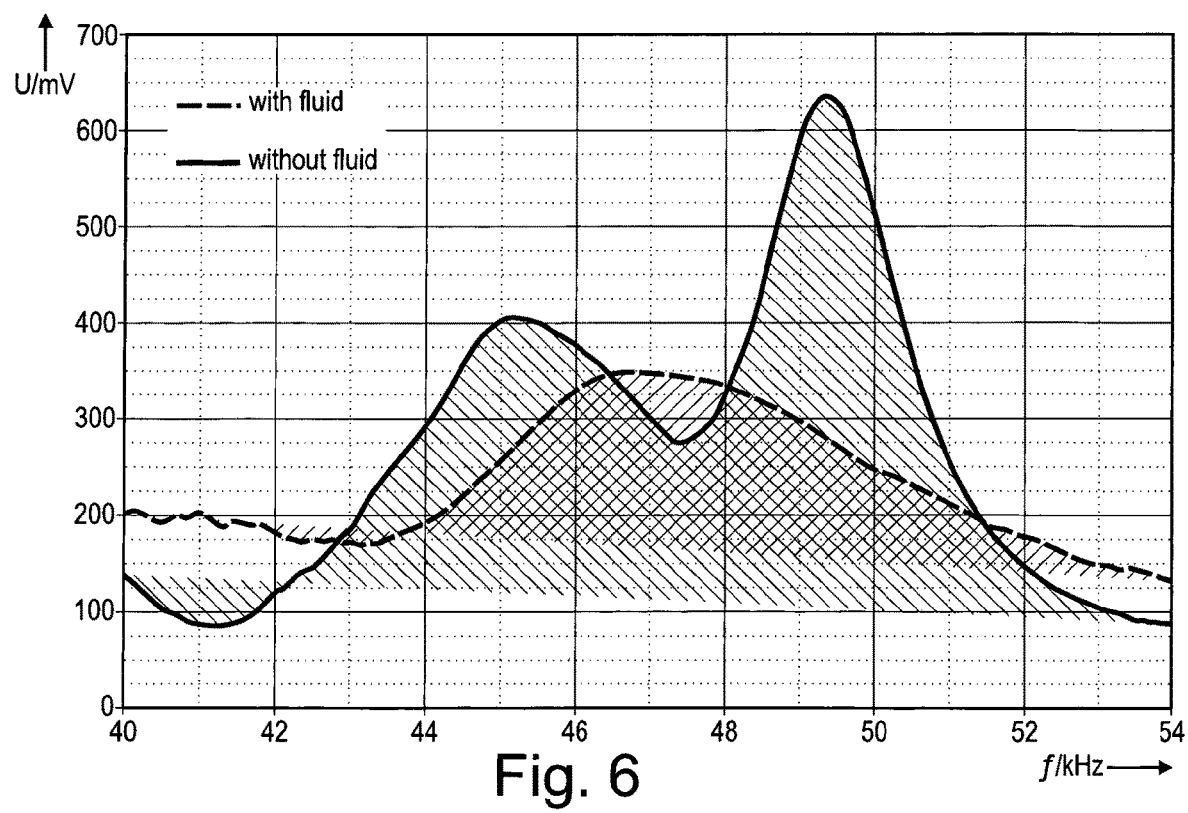
FIG. 6 shows a diagram of the voltage of the vibrator of the aerosol delivery device shown in FIG. 1, presenting two curves of the detected voltage values, one with fluid and the other without fluid, and indicating the areas under the curves.

FIG. 6 illustrates an embodiment of the present invention in which the presence of fluid 3 in contact with the membrane 1 is detected on the basis of the area under a curve of the detected values of the at least one electrical parameter of the vibrator 7 as a function of the vibration frequency. In this embodiment, the at least one electrical parameter is the voltage of the vibrator 7. However, the present invention is not limited thereto.

FIG. 6 shows two measured voltage curves in the frequency range from 40 to 54 kHz, wherein one curve was measured for the case that fluid 3 in contact with the membrane 1 was present and the other curve was measured for the case that no fluid 3 in contact with the membrane 1 was present.

As is indicated by grey-shaded areas in FIG. 6, the area under the curve is defined in this embodiment as the area between the curve and a straight line connecting the first measured point of the curve with the last measured point of the curve. The area under the curve, i.e., below or underneath the curve, is determined or calculated by the processor, such as a CPU or the like, which forms part of the detector 13*a*. The area thus obtained is compared with one or more reference area values which are stored in the detector 13*a*, e.g. in a memory thereof. This comparison is also performed by the processor of the detector 13*a*.

The one or more reference area values may be obtained from previous measurements, e.g. reference measurements, for example, by averaging a plurality of measurements and determining or calculating the area under the averaged curve thus obtained. Alternatively, the one or more reference area values may be empirically determined.

For example, the area under the measured voltage curve may be compared with two reference area values, one obtained for the case that fluid 3 in contact with the membrane 1 is present and the other obtained for the case that no fluid 3 in contact with the membrane 1 is present.

On the basis of the comparison of the determined area under the measured voltage curve with the one or more reference area values, the presence of fluid 3 in contact with the membrane 1 can be reliably and efficiently detected. The probability of the detection error of the first type was found to be less than 1%. Therefore, an undesired deactivation of the vibrator 7 for the case that fluid 3 in contact with the membrane 1 is still present can be reliably prevented.

Figure 7:
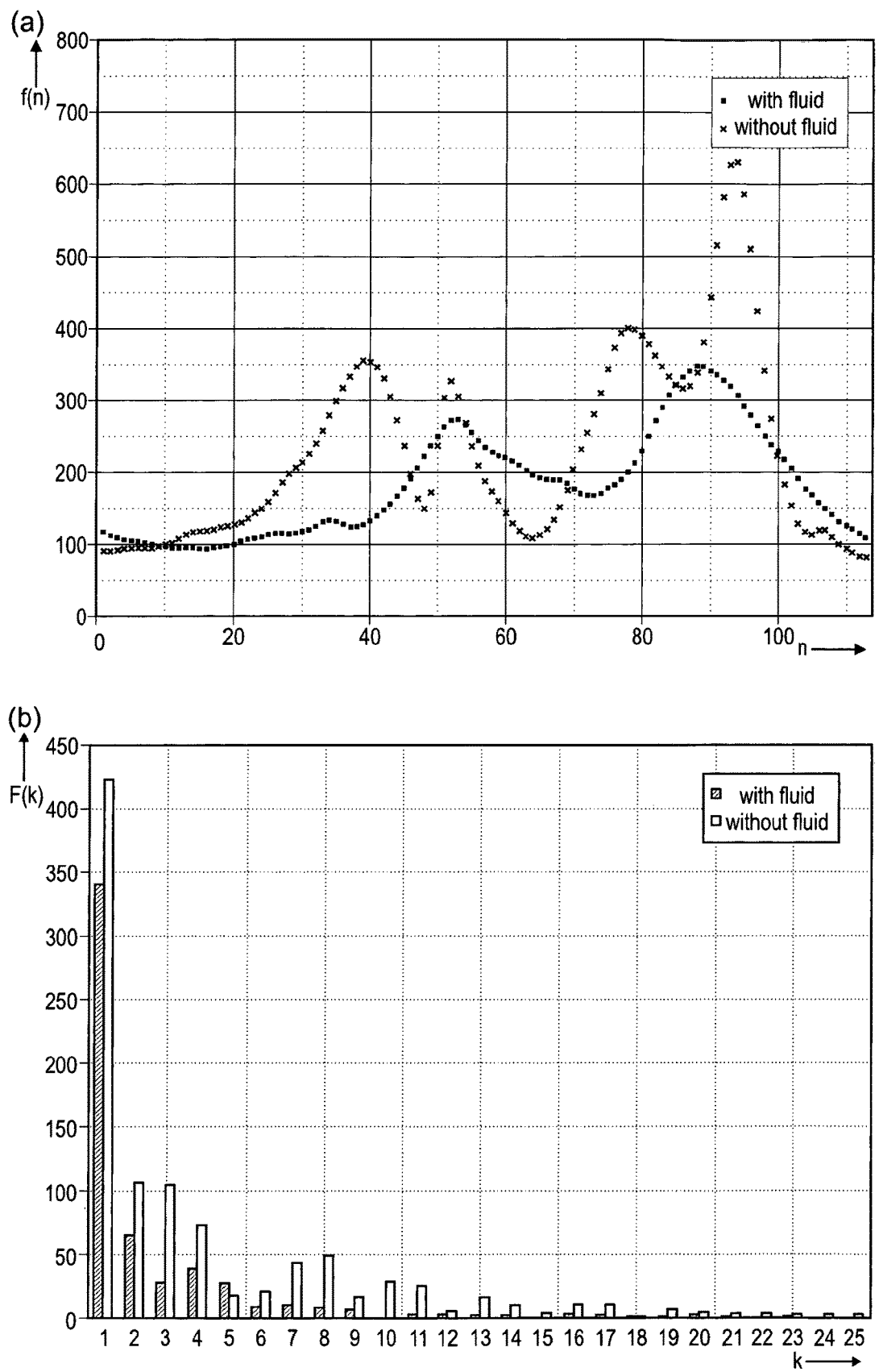

FIG. 7 illustrates an embodiment of the present invention in which the presence of fluid 3 in contact with the membrane 1 is detected on the basis of a Fourier transform of a curve of the detected values of the at least one electrical parameter of the vibrator 7 as a function of the vibration frequency. In this embodiment, the at least one electrical parameter is the voltage of the vibrator 7. However, the present invention is not limited thereto.

FIG. 7(*a*) shows two measured curves of the voltage of the vibrator 7 as dependent on the vibration frequency in the frequency range from 30 to 55 kHz, wherein one curve was measured with fluid 3 in contact with the membrane 1 and the other curve was measured without fluid 3 in contact with the membrane 1. The measured voltage of the vibrator 7 is given on the Y-axis (ordinate) of FIG. 7(*a*) as f(n) and the parameter n given on the X-axis (abscissa) of FIG. 7(*a*) is an integer. The curves shown in FIG. 7(*a*) were subjected to low pass filtering in order to filter out high-frequency background noise.

The curves of FIG. 7(*a*), showing the measured signal in the time area or time region, were Fourier transformed into the spectral region or spectral area, thereby obtaining the Fourier transform shown in FIG. 7(*b*). FIG. 7(*b*) shows the intensity F(k) on the Y-axis and the integer k on the X-axis.

It was found that the curves taken without fluid 3 in contact with the membrane 1 have higher-frequency portions than the curves taken with fluid 3 in contact with the membrane 1. Hence, the presence of fluid 3 in contact with the membrane 1 can be reliably and efficiently detected by identifying these portions.

For this purpose, the intensities F(k) are added up for a plurality of values of k, e.g., 10, 20, 30 or 40 values of k, in order to determine the high-frequency portions of the measured signals. For example, the intensities F(k) may be added up from k=0 to k=10, from k=1 to k=11 or from k=2 to k=12.

The sum of the intensity values thus obtained is compared with one or more reference intensity values which are stored in the detector 13*a*, e.g. in a memory thereof. The Fourier transformation of the measured curves and the comparison of the determined sum of the intensity values with the one or more reference intensity values is performed by the processor, such as e.g. a CPU or the like, which is part of the detector 13*a*.

The one or more reference intensity values may be obtained from previous measurements, e.g. from single measurements or from averages taken from a plurality of measurements. Alternatively, the one or more reference intensity values may be empirically determined.

On the basis of the comparison of the determined sum of the intensity values with the one or more reference intensity values, the presence of fluid 3 in contact with the membrane 1 can be detected in a reliable and efficient manner. In particular, the probability of the detection error of the first type was found to be less than 1%. Alternatively, the probability of the detection error of the first type was found to be less than 0.5% or even less than 0.1%. Hence, an undesired deactivation of the vibrator 7 in the case that fluid 3 in contact with the membrane 1 is still present can be reliably prevented.

The foregoing embodiments and their variants have been disclosed for illustrative purposes only, and further variation is wholly possible within the capabilities of the skilled reader. Accordingly, the appended claims are intended to cover all modifications, substitutions, alterations, omissions and additions which one skilled in the art could achieve from the foregoing disclosure, taking into account his own general and specialist knowledge and expertise.

The invention claimed is:

1. An aerosol delivery device comprising:
    an aerosol generator for generating an aerosol in the aerosol delivery device, the aerosol generator comprising
        a membrane, and
        a vibrator, which is configured to vibrate a fluid and to aerosolise the fluid by the membrane,
    a fluid reservoir for receiving the fluid to be aerosolised, the fluid reservoir being arranged in fluid communication with the membrane,
    a controller which is configured to sequentially operate the vibrator at a plurality of different vibration frequencies,
    a sensor which is configured to detect at least one electrical parameter of the vibrator for each of the plurality of different vibration frequencies, and
    a detector which is configured to detect the presence of the fluid in contact with the membrane on the basis of the dependence of the detected values of the at least one electrical parameter on the vibration frequency, wherein the detector is configured to detect the presence of the fluid in contact with the membrane on the basis of a slope or slopes of a curve of the detected values of the at least one electrical parameter as a function of the vibration frequency and on the basis of a length of the curve, wherein the at least one electrical parameter is a voltage and/or a current and/or a power and/or a current/voltage phase shift.

2. The aerosol delivery device according to claim 1, wherein the detector is configured to detect the presence of the fluid in contact with the membrane on the basis of a cross correlation of a curve of the detected values of the at least one electrical parameter as a function of the vibration frequency with a reference curve.

3. The aerosol delivery device according to claim 1, wherein the detector is configured to detect the presence of the fluid in contact with the membrane on the basis of the difference obtained by subtracting a curve of the detected values of the at least one electrical parameter as a function of the vibration frequency obtained in one detection cycle from a curve of the detected values of the at least one electrical parameter as a function of the vibration frequency obtained in another detection cycle.

4. The aerosol delivery device according to claim 1, wherein the detector is configured to detect the presence of the fluid in contact with the membrane on the basis of an area under a curve of the detected values of the at least one electrical parameter as a function of the vibration frequency.

5. The aerosol delivery device according to claim 1, wherein the detector is configured to detect the presence of the fluid in contact with the membrane on the basis of a Fourier transform of a curve of the detected values of the at least one electrical parameter as a function of the vibration frequency.

6. The aerosol delivery device according to claim 1, wherein the controller is configured to deactivate the vibrator if no presence of the fluid in contact with the membrane is detected by the detector.

7. The aerosol delivery device according to claim 1, wherein the controller is configured to sequentially operate the vibrator at 40 or more different vibration frequencies of the plurality of different vibration frequencies.

8. The aerosol delivery device according to claim 1, wherein the controller is configured to switch the vibrator from one vibration frequency to the next vibration frequency of the plurality of different vibration frequencies within a time period of 20 ms or less.

9. The aerosol delivery device according to claim 1, wherein the controller is configured to sequentially operate the vibrator at the plurality of different vibration frequencies in the range of 30 to 60 kHz and/or 90 to 170 kHz and/or 350 to 600 kHz.

10. The aerosol delivery device according to claim 1, wherein the controller is configured to sequentially operate the vibrator at the plurality of different vibration frequencies so that the difference between one vibration frequency and the next vibration frequency is not more than 3% of the one vibration frequency.

11. The aerosol delivery device according to claim 1, wherein the controller is configured to sequentially operate the vibrator at the plurality of different vibration frequencies so that the difference between one vibration frequency and the next vibration frequency is a function of the vibration frequencies.

12. The aerosol delivery device according to claim 1, wherein the membrane is a passive membrane and the vibrator is configured to vibrate a fluid supply system and/or a membrane back space of the aerosol delivery device.

13. The aerosol delivery device according to claim 1, wherein the membrane is an active membrane and the vibrator is configured to vibrate the membrane.

14. A method of operating an aerosol delivery device, the aerosol delivery device comprising:
    an aerosol generator for generating an aerosol in the aerosol delivery device, the aerosol generator comprising
        a membrane, and
        a vibrator which is configured to vibrate a fluid and to aerosolise the fluid by the membrane,
    and
    a fluid reservoir for receiving the fluid to be aerosolised, the fluid reservoir being arranged in fluid communication with the membrane,
    the method comprising the steps of:
        sequentially operating the vibrator at a plurality of different vibration frequencies,
        detecting at least one electrical parameter of the vibrator for each of the plurality of different vibration frequencies, and
        detecting the presence of the fluid in contact with the membrane on the basis of the dependence of the detected values of the at least one electrical parameter on the vibration frequency, wherein the presence of the fluid in contact with the membrane is detected on the basis of a slope or slopes of a curve of the detected values of the at least one electrical parameter as a function of the vibration frequency and on the basis of a length of the curve, wherein the at least one electrical parameter is a voltage and/or a current and/or a power and/or a current/voltage phase shift.

15. The method of operating an aerosol delivery device according to claim 14, wherein the membrane is a passive membrane and the vibrator is configured to vibrate a fluid supply system and/or a membrane back space of the aerosol delivery device.

16. The method of operating an aerosol delivery device according to claim 14, wherein the membrane is an active membrane and the vibrator is configured to vibrate the membrane.

17. The method of operating an aerosol delivery device according to claim 14, wherein the fluid to be aerosolised contains one or more active agents, the one or more active agents being selected from the group consisting of an anti-epileptic drug, an anti-convulsive drug, an anti-emetic, a immunemodulator, a pain killer, an anti-rheumatic, an anti-cancer drug, a mucolytic drug, a sleeping assistant, an anti-mycotic, a sexual stimulant, a protein or peptide, heparane and a gene, and/or the group consisting of an anti-diabetic drug, insulin and a hormone, and/or the group consisting of a corticosteroid, a leukotriene antagonist, a bradykinin antagonist, a cromone, an anti-histamine and an antibody, and/or the group consisting of an aminoglycoside, a cephalosporine, a macrolide, a chonolone, a nitroimidazol, a glycopeptide, a polyen-antibiotic, a beta-lactam, a tetracycline, a quinolone, a sulfonamide, and an azol derivative, and/or the group consisting of a benzodiazepine, a barbitute and a succinimide, and/or the group consisting of alpha antitrypsine, erythropoetine, interferones, kinases, elastases, peptides and proteines, and/or the group consisting of salbutamol, levalbuterol, formoterol, fenoterol, salmeterol, bambuterol, brocaterol, clenbuterol, terbutalin, tulobuterol, epinephrin, isoprenalin, and hexoprenalin, and/or the group consisting of tiotropium, oxitropium, ipratropium, and glcopyrrolate, and/or the group consisting of acetylcystein, ambroxol, carbocystein, tyloxapol, dipalmytoylphosphatidylcholin, recombinant surfactant proteins, and D-Nase, and/or the group consisting of surfactants, and/or the group consisting of cromoglycate, nedocromil, beclomethasone, betamethasone, budesonide, ciclesonide, flunisolide, fluticasone, icomethasone, mometasone, rofleponide, triamcinolone, bradykinine-, prostaglandine-, leucotriene- and platelet activating factor antagonists, and/or the group consisting of amoxycillan, piperacillin, clavulan acid, sulbactam, cefaclor, cefazedon, Cefuroxim, Cefoxitin, cefodizim, cefsulodin, cefpodixim, cefixim, colistin, imipenem, cilastatin, aztrenonam, streptomycin, neomycin, paromomycin, kanamycin, gentamycin, amicacin, tobramycin, spectinomycine, doxycyclin, minocycline, erythromycine, clarithromycine, roxithromycine, azithromycine, josamycine, spiramycine, Ciprofloxacin, Ofloxacine, Levofloxacine, pefloxacine, lomefloxacine, flexoxacine, clinafloxacine, sitafloxacine, gemifloxacine, balofloxacine, trovafloxacine, moxifloxacine, metronidazol, tinidazol, chloramphenicol, lincomycine, clindamycine, fosfomycine, vancomycine and teicoplanine, and/or the group consisting of refampicine, isoniacide, cycloserine, terizidone, and ansamycine, and/or the group consisting of clotrimazol, oxiconazol, miconazol, ketoconazol, itraconazol, fluconazol, amphotericine B, natamycine, nystatine, flucytosine, and Pentamidine, and/or the group consisting of dimepranol-4-acetate amideo benzoate, thymopentin, interfer-ones, filgrastine, interleukine, azathioprine, and cyclosporine; virustatics such as podophyllotoxine, vidarabine, tromantadine, zidovudine, and a-antitrypsin, and/or the group consisting of corticotro-pine, tetracosactide, choriogonandotropine, urofolitropine, urogonadotropine, saomatotropine, metergoline, desmopres sine, oxytocine, argipressine, or-nipressine, leuproreline, triptoreline, gonadoreline, busereline, nafareline, goselerine, somatostatine, parathyroide gland hormones, Dihydrotachysterole, calcitonine, clodron acid, etidron acid, thyroid gland therapeutics, anabolics, androgens, etrogens, gestagenes, and antiestrogenes, and/or the group consisting of nimustine, melphanlane, carmustine, lomustine, cyclophosphosphamide, ifosfamide, trofosfamide, chlorambucil, busulfane, treosulfane, prednismustine, thiotepa, cytarabine, fluorouracil, mercaptopurine, tioguanine, vinblastine, vincristine, vindesine, alcarubicine, bleomycine, dactinomycine, daunorubicine, doxorubicine, epirubicine, idarubicine, mitomycine, plicamycine, carboplatinum, cis-platinum, titanocendichloride Amsacrine, dacarbazine, estramustine, etoposide, hydroxycarbamide, mitoxanthrone, procarbazine, and temiposide, and/or the group consisting of Proxibarbal, lisuride, methysergide, dihydroergotamine, ergotamine, clonidine, pizotifene, bezodiazepines, barbiturates, cyclopyrrolones, imidazopyridines, arbiturates, Pheytoin, Primidone, mesuximide, ethosuximide, sultiam, carbamezepin, valproic acid, vigabatrine, Levodopa, carbidopa, benserazide, selegiline, bromocriptine, amantadine, tiapride, Thiethylperazine, bromopride, domperidone, granisetrone, ondasetrone, tropisetrone, pyridoxine, morphine, codeine, hydromorphone, methadone, fenpipramide, fentanyl, piritramide, pentazocine, buprenorphine, nalbuphine, tilidine, N-methylated barbiturates, thiobarbiturates, ketamine, etomidate, propofol, benzodiazepines, droperidol, haloperidol, alfentanyl, sulfentanyl, tumor necrosis factor alpha and non-steroidal antiinflammatory drugs, and/or the group consisting of insulin, sulfonylurea derivatives, biguanids, glitizols, glucagon, diazoxid, interleukines, interferones, tumor necrosisfactor (TN F), and colony stimulating factors, and/or the group consisting of proteins, peptides, heparine, heparinoids, urokinases, streptokinases, ATP-ase, prostacycline, sexual stimulants, and genes.

18. The method of operating an aerosol delivery device according to claim 14, wherein the fluid to be aerosolised contains one or more active agents including monobactams.

19. The method of operating an aerosol delivery device according to claim 14, wherein the fluid to be aerosolised contains one or more active agents including aztreonam.

* * * * *